(12) United States Patent
Yang et al.

(10) Patent No.: US 11,007,116 B2
(45) Date of Patent: May 18, 2021

(54) MEDICANT DISPENSER FOR THE PREVENTION INFILTRATION FROM BACTERIA

(71) Applicants: Kyung Ok Yang, Yongin-si (KR); Su Yong Kim, Hwaseong-si (KR); Jae Young Yang, Hwaseong-si (KR)

(72) Inventors: Kyung Ok Yang, Yongin-si (KR); Su Yong Kim, Hwaseong-si (KR); Jae Young Yang, Hwaseong-si (KR)

( * ) Notice: Subject to any disclaimer, the term of this patent is extended or adjusted under 35 U.S.C. 154(b) by 211 days.

(21) Appl. No.: 16/222,527

(22) Filed: Dec. 17, 2018

(65) Prior Publication Data
US 2020/0009014 A1   Jan. 9, 2020

(30) Foreign Application Priority Data

Jul. 9, 2018   (KR) .......................... 10-2018-0079274

(51) Int. Cl.
*B65D 47/18*   (2006.01)
*A61J 1/14*   (2006.01)
(Continued)

(52) U.S. Cl.
CPC ........... *A61J 1/1443* (2013.01); *A61F 9/0008* (2013.01); *A61M 39/24* (2013.01); *B65D 47/18* (2013.01);
(Continued)

(58) Field of Classification Search
CPC ..... A61J 1/1443; A61F 9/0008; A61M 39/24; A61M 2039/2473; A61M 2039/2493; B65D 47/18; B05B 11/00444; B05B 11/3001
See application file for complete search history.

(56) References Cited

U.S. PATENT DOCUMENTS

2004/0200860 A1* 10/2004 Buxmann ........... B05B 11/3042
                                                    222/321.6
2006/0011663 A1*  1/2006 Greiner-Perth ..... B05B 11/3092
                                                    222/383.1
(Continued)

FOREIGN PATENT DOCUMENTS

EP        2992967 A1    3/2016
JP     2008-514891 A    5/2008
(Continued)

OTHER PUBLICATIONS

English Translation of KR 10-1551191 (published as published as KR20140-14158A) Specification (Year: 2015).*

*Primary Examiner* — Ariana Zimbouski
(74) *Attorney, Agent, or Firm* — Novick, Kim & Lee, PLLC; Jae Youn Kim

(57) ABSTRACT

Provided is a medication dispenser configured to discharge a liquid state medication stored therein by a pumping operation in a predetermined amount in a drop state and prevent a noise occurrence during medication discharge, and having a bacteria infiltration prevention function, wherein a flow path member and a second check valve are mounted in a liner, the second check valve is composed of a hemispherical cylinder mounted in an elevation space of the liner, having an open upper part, and of which a diameter decreases toward a lower end and includes a variable part in which the hemispherical cylinder is vertically variable and an opening and closing protrusion configured to perform supply and blocking of a flow path.

5 Claims, 28 Drawing Sheets

(51) Int. Cl.
*A61F 9/00* (2006.01)
*A61M 39/24* (2006.01)

(52) U.S. Cl.
CPC ............... *A61M 2039/2473* (2013.01); *A61M 2039/2493* (2013.01)

(56) References Cited

U.S. PATENT DOCUMENTS

| | | | | |
|---|---|---|---|---|
| 2012/0197219 | A1* | 8/2012 | Scanlon | B05B 11/3094 604/295 |
| 2014/0301875 | A1* | 10/2014 | Lee | B05B 11/305 417/534 |
| 2017/0291183 | A1* | 10/2017 | Lee | B05B 11/305 |

FOREIGN PATENT DOCUMENTS

| | | |
|---|---|---|
| JP | 2008-173474 A | 7/2008 |
| JP | 2013-504355 A | 2/2013 |
| JP | 2014-180664 A | 9/2014 |
| JP | 2014-193338 A | 10/2014 |
| KR | 10-1457173 B1 | 10/2014 |
| KR | 2014-0146680 A | 12/2014 |
| KR | 10-1550698 B1 | 9/2015 |
| KR | 10-1551191 B1 | 9/2015 |

* cited by examiner

MEDICANT DISPENSER FOR THE PREVENTION INFILTRATION FROM BACTERIA

CROSS-REFERENCE TO RELATED APPLICATION

This application claims priority to and the benefit of Korean Patent Application No. 10-2018-0079274, filed on Jul. 9, 2018, the disclosure of which is incorporated herein by reference in its entirety.

BACKGROUND

1. Field of the Invention

The present disclosure relates to a medication dispenser configured to discharge a liquid state medication, which is stored therein by a pumping operation, in a predetermined amount in a drop state and prevent noise generation during medication discharge, and having a bacteria infiltration prevention function.

2. Discussion of Related Art

Generally, a dispenser is an apparatus configured to discharge and use gas, liquid, or other contents filled in a sealed container in a predetermined amount by a pressure, and applied to various sealed containers configured to store cosmetics, a perfume, a drug, food or the like.

The above-described dispenser is mounted on an upper end of the container and includes a pumping part, a button part, and a nozzle, and when the button part is pushed, since a shaft descends against an elastic force of a spring, the contents filled in a housing are discharged to a nozzle through a through hole and a hollow part and a connection pipe of the shaft. In this case, a ball comes into contact with an engaging protrusion of a lower end of the housing due to a descending pressure of a fluid in the housing. Further, when the button part is released, since the shaft ascends due to the elastic force of the spring, the through hole is closed and discharge of the contents is prevented, and since a vacuum is formed in the housing, the contents filled in the container lift the ball and open a valve to be filled in the housing.

When the above-described button part is repeatedly pushed, the contents are discharged while the above-described operation is repeated. However, since a dispenser according to the related art has a metal ball, production costs increase, and since a valve structure including the ball is provided and thus an additional post-processing process should be performed, a manufacturing process is complicated and workability of the manufacturing process is reduced.

Further, in the dispenser according to the related art, since the contents remain in the nozzle, and thus the remaining contents come into contact with air and moisture is evaporated and coagulates, the contents are spoiled and the nozzle is blocked.

Technologies for solving the above-described problems are disclosed in the following documents 1 to 3.

For example, Patent Document 1 (Korean Patent Laid-Open No. 10-1457173, Oct. 27, 2014) discloses a medication dispenser configured to prevent introduction of external dirt, foreign substances, or bacteria into the medication stored therein, the medication dispenser including a suction part coupled to an upper part of a container and configured to suction a liquid state medication stored in the container, a pumping part coupled to one side of the suction part and configured to perform a pumping operation to inject the medication in a predetermined amount, and an injection part installed on an upper end of the pumping part and having an injection hole in a front end thereof, wherein the pumping part includes a piston configured to perform an elevation operation according to an elevation operation of the injection part, a valve stem connected to a lower end of the piston, and an elastic member coupled to the outside of the valve stem to provide a restoring force to the injection part.

Further, Patent Document 2 (Korean Patent Laid-Open No. 10-1550698, Sep. 1, 2015) discloses a medication dispenser including a suction part coupled to an upper part of a container and configured to suction a liquid state medication stored in the container, a pumping part coupled to one side of the suction part to perform a pumping operation to discharge the medication in a predetermined amount, and a discharge part installed on an upper end of the pumping part and having a discharge hole configured to discharge the medication in a drop state at a front end thereof, wherein the pumping part blocks introduction of external dirt, foreign substances, or bacteria into the medication stored therein, and the suction part includes a coupling cylinder coupled to an upper end of the container, a housing coupled to a lower part of the coupling cylinder and having an introduction port into which the medication stored in the container is introduced, and a check valve installed at a lower part of the housing to open and close the introduction port.

Meanwhile, Patent Document 3 (Korean Patent Laid-Open No. 10-1551191, Sep. 2, 2015) discloses a medication dispenser including a suction part coupled to an upper part of a container and configured to suction a liquid state medication stored in the container, a pumping part coupled to one side of the suction part to perform a pumping operation to inject the medication in a predetermined amount, and an injection part installed on an upper end of the pumping part and having an injection hole in a front end thereof, wherein the injection part includes a head base having the injection hole formed in an upper end thereof, a liner installed in the injection path formed in the head base and configured to transfer the medication pumped by an elevation operation of a piston to the injection hole, and a vortex forming part configured to form a vortex in the medication transferred to the injection hole, and a moving path configured to move the medication transferred by the pumping operation of the pumping part to the injection hole and a rotating path configured to rotate the medication which moves through the moving path along an outer circumferential surface of the liner and transfer the medication to the injection hole are formed in the outer circumferential surface of the liner.

SUMMARY OF THE INVENTION

However, according to a result of repeated tests by inventors of the present disclosure, in the technologies disclosed in the above-described Patent Documents, since a check valve moves when a valve sheet is vertically operated, a pumping error occurs, a noise is generated when a medication is discharged, and a discharging amount is not steadily maintained.

Further, since an inlet of a valve stem is broadly provided in the technologies disclosed in the Patent Documents, initial discharge of the medication is uncertainly performed, and a pumping error occurs during repeated pumping.

In addition, since a spring and a piston are applied to a discharge part in the technologies disclosed in the Patent Documents, operation impossibility due to a backflow of the medication and a defect of the spring increases and since a strong spring is used for a pumping operation, a pumping sensation becomes worse.

Meanwhile, in the Patent Document 2, since a plurality of adjusting protrusions configured to adjust an amount of the medication discharged to the discharge part are provided to protrude, foreign substances and bacteria are introduced, and since an adjusting groove of a suction part is formed in a rectangular shape, a discharging amount is not steadily maintained.

The present disclosure is directed to providing a medication dispenser configured to accurately perform a pumping operation and prevent noise generation and having a bacteria infiltration prevention function.

Also, the present disclosure is directed to providing a medication dispenser configured to certainly perform initial discharge of a medication and prevent an occurrence of an error during repeated pumping.

Also, the present disclosure is directed to providing a medication dispenser configured to prevent a back flow of the medication and improve a pumping sensation.

Also, the present disclosure is directed to providing a medication dispenser configured to prevent introduction of foreign substances and bacteria and steadily maintain a discharging amount of the medication.

According to an aspect of the present disclosure, there is provided a medication dispenser having a bacteria infiltration prevention function including a suction part coupled to an upper part of a container and configured to suction a liquid state medication stored in the container, a pumping part coupled to one side of the suction part to perform a pumping operation to discharge the medication in a predetermined amount, a discharge part installed on an upper end of the pumping part and having a discharge hole configured to discharge the medication in a drop state in a front end thereof, and a cover part configured to cover the discharge part, wherein the discharge part includes a head base into which the cover part is inserted and a liner inserted into the head base and to which an upper part of a valve stem is fitted, the suction part includes a coupling cylinder coupled to an upper end of the container, a housing coupled to a lower part of the coupling cylinder, and a first check valve installed at a lower part of the housing to open and close an introduction port in which the medication is introduced into the housing, a valve sheet configured to open or close the introduction port is provided at a center portion of the inside of the first check valve and connected to a main body by a plurality of connection ribs each having a concave part at a center portion of an upper part, the liner has a flow path member and a second check valve mounted therein and a discharge hole formed of three separation films each formed at an interval of 120° is provided in an upper part of the liner, the second check valve is composed of a hemispherical cylinder mounted in an elevation space of the liner, having an open upper part, and of which a diameter decreases toward a lower end and includes a variable part in which the hemispherical cylinder is vertically variable and an opening and closing protrusion configured to perform supply and blocking of a flow path, the flow path member has a supporting plate formed in a disk shape to be engaged with a ring-shaped engaging protrusion of the second check valve at a bottom part of a flow path space of the liner, a first induction part provided on the supporting plate in a cylindrical shape, and a second induction part provided on the first induction part in a cylindrical shape, and first to fifth induction paths are provided in the first induction part and the second induction part.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION OF EXEMPLARY EMBODIMENTS

The above-described and other purposes and new characteristics of the present disclosure will be more apparent by a technology and the accompanying drawings in the description.

A term "pumping" used in the present disclosure refers to a process in which a medication provided in a container by an operation of a pumping part is discharged to the outside of the dispenser, and a term "pumping error" means non-uniform discharge of the medication.

Further, a term "ascending" used in the present disclosure refers to upward movement when the medication dispenser is used in a normal state but also refers to downward movement when the medication dispenser is used in reverse. In addition, a term "descending" refers to downward movement when the medication dispenser is used in the normal state but also refers to upward movement when the medication dispenser is used in reverse.

Here, an embodiment according to the present disclosure will be described on the basis of the drawings.

Figure 1:
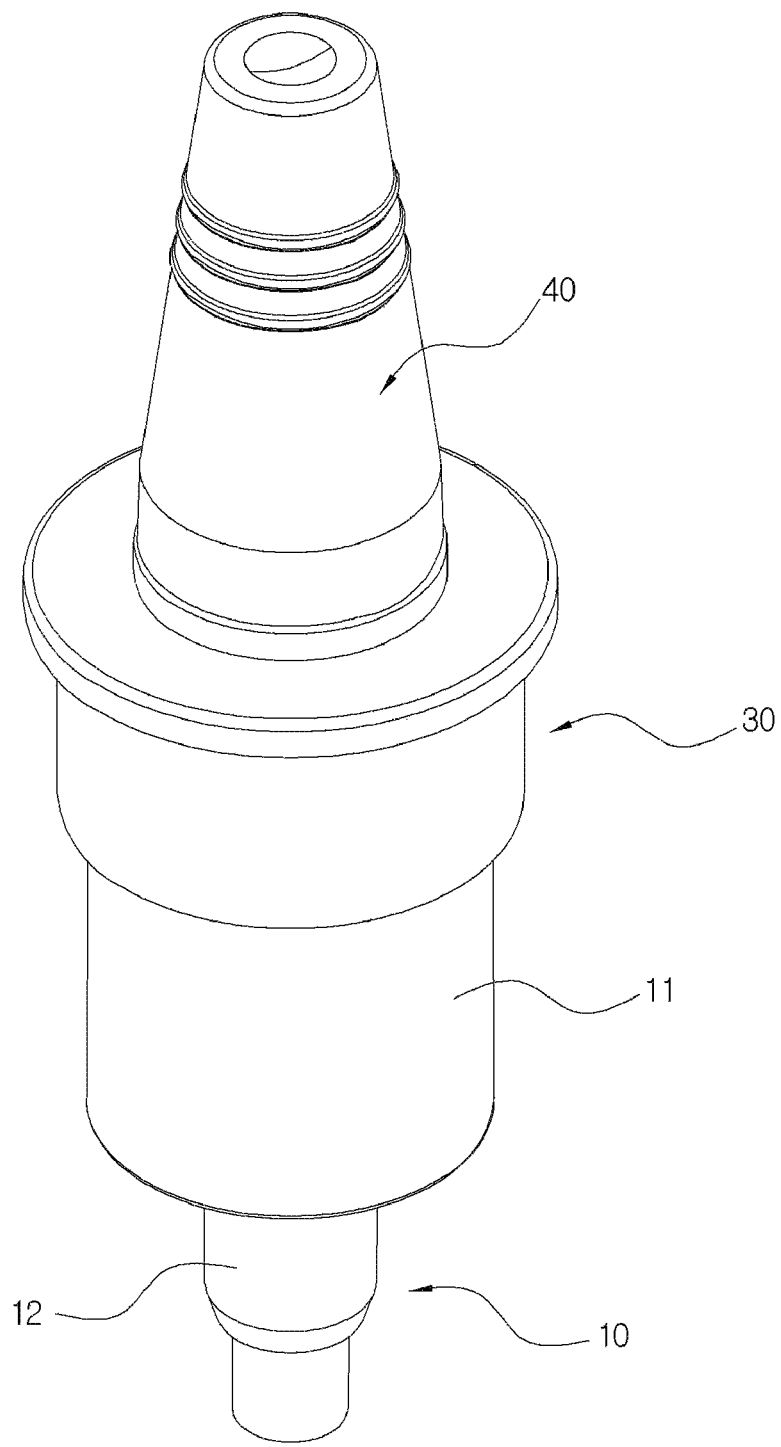
FIG. 1 is a perspective view of a medication dispenser having a bacteria infiltration prevention function according to the present disclosure.
Figure 2:
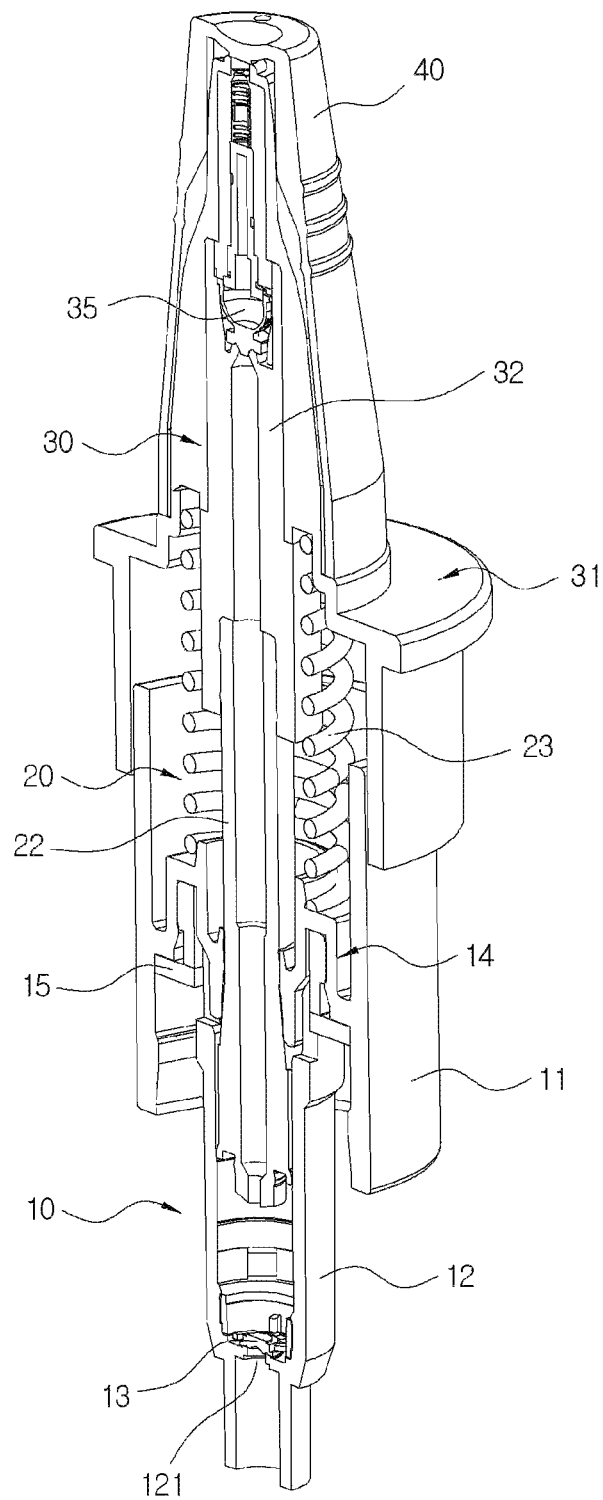
FIG. 2 is a view illustrating a state of the inside of the medication dispenser shown in FIG. 1.
Figure 3:
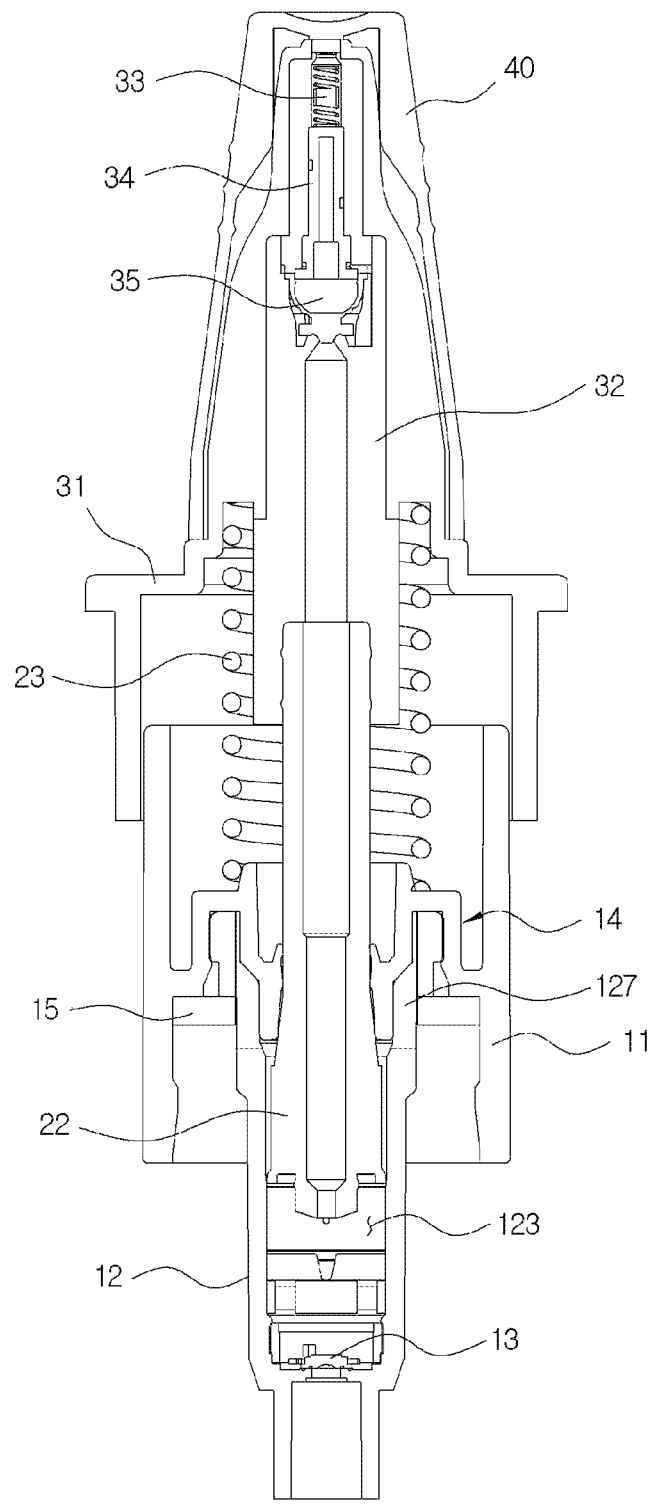
FIG. 3 is a cross-sectional view of the medication dispenser shown in FIG. 1.
Figure 4:
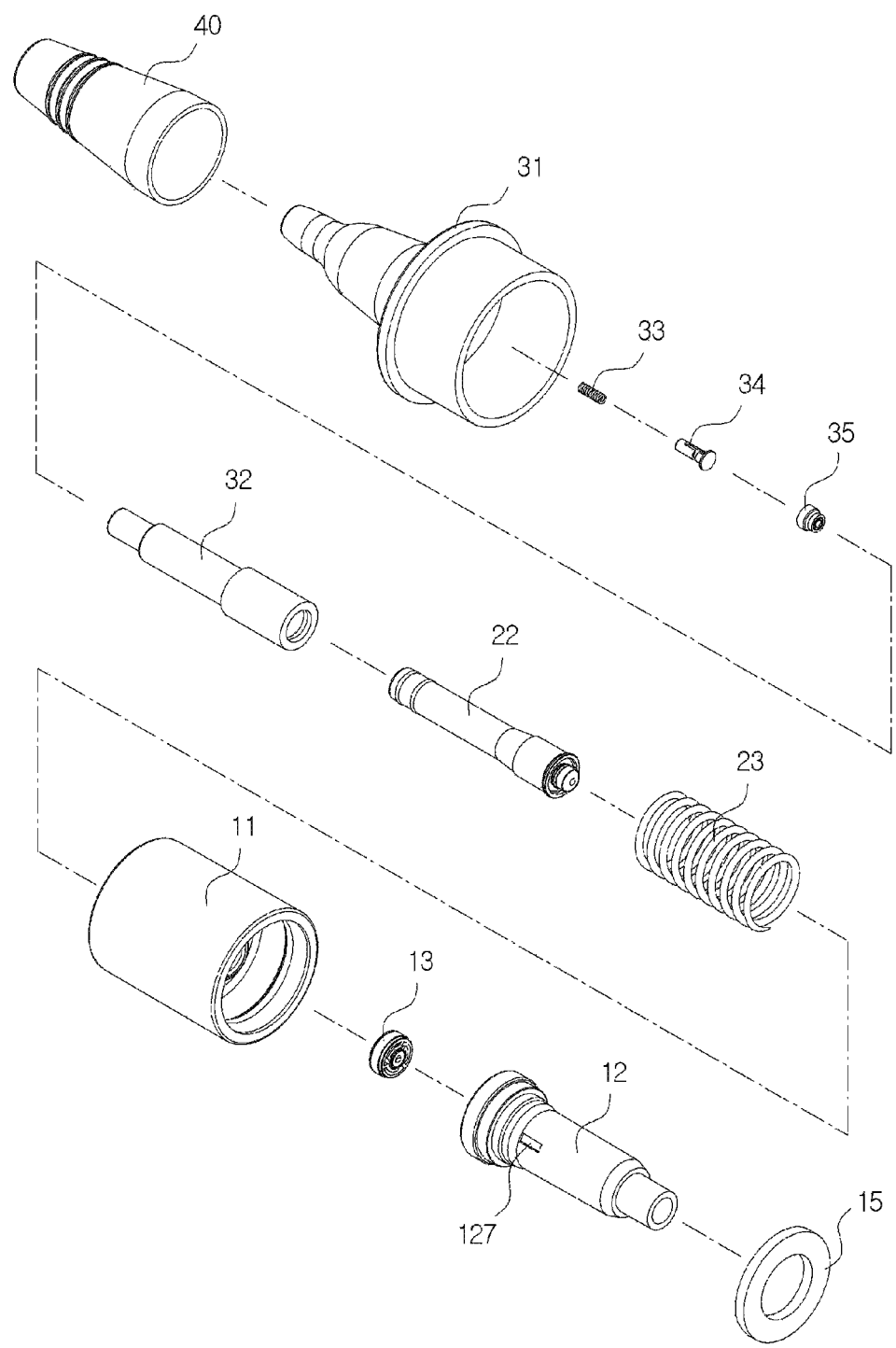
FIG. 4 is an exploded perspective view of the medication dispenser shown in FIG. 1.

FIG. 1 is a perspective view of a medication dispenser having a bacteria infiltration prevention function according to the present disclosure, FIG. 2 is a view illustrating a state of the inside of the medication dispenser shown in FIG. 1, FIG. 3 is a cross-sectional view of the medication dispenser shown in FIG. 1, and FIG. 4 is an exploded perspective view of the medication dispenser shown in FIG. 1.

As shown in FIGS. 1 and 2, the medication dispenser having a bacteria infiltration prevention function according to an exemplary embodiment of the disclosure includes a suction part 10 coupled to an upper part of a container (not shown in the drawings) and configured to suction the medication stored in the container, a pumping part 20 coupled to one side of the suction part 10 and configured to perform a pumping operation to discharge the medication in a drop state and in a predetermined amount, a discharge part 30 installed on an upper end of the pumping part 20 and having a discharge hole 312 in a front end thereof, and a cover part 40 configured to cover the discharge part 30.

As shown in FIGS. 2 and 3, the suction part 10 may include a coupling cylinder 11 coupled to an upper end of the container, a housing 12 coupled to a lower part of the coupling cylinder 11, and a first check valve 13 installed at a lower part of the housing 12 to open and close an introduction port 121 through which the medication is introduced into the housing 12.

As shown in FIGS. 2 and 4, the pumping part 20 may include a valve stem 22, which is fitted to the housing 12, and an elastic member 23 configured to raise the valve stem 22.

The discharge part 30 may include a head base 31, into which the cover part 40 is inserted, and a liner 32 inserted into the head base 31 and to which an upper part of the valve stem 22 is fitted. As shown in FIG. 4, a pollution prevention member 33, a flow path member 34, and a second check valve 35 provided in a discharge path and configured to prevent pollution of the remaining medication in a discharge hole 323 are mounted in the liner 32.

Figure 5:
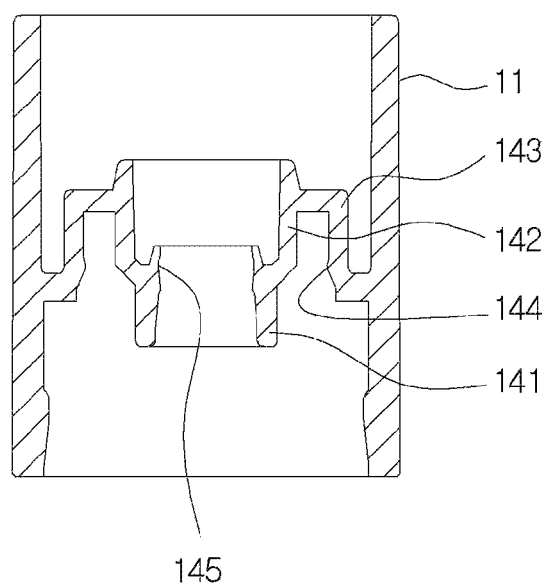
FIG. 5 is a cross-sectional view of a coupling cylinder for describing a configuration of a guide member according to the present disclosure.

As shown in FIGS. 1 and 2, the coupling cylinder 11 is formed in a roughly cylindrical shape, and as shown in FIG. 5, a guide member 14 configured to guide an elevation operation of the valve stem 22 provided in the pumping part 20 is installed in the coupling cylinder 11.

FIG. 5 is a cross-sectional view of the coupling cylinder 11 for describing a configuration of the guide member 14 according to the present disclosure.

As shown in FIG. 5, the guide member 14 is formed in a roughly cylindrical shape of which upper and lower surfaces are open and may include a first coupling guide 141 to which a lower end portion of the valve stem 22 is inserted and coupled, a second coupling guide 142 formed to be connected to an upper part of the first coupling guide 141, and a connection member 143 configured to connect the second coupling guide 142 and the coupling cylinder 11.

The first coupling guide 141 serves to guide the elevation operation of the valve stem 22 coupled to the inside thereof. To this end, the first coupling guide 141 may be formed to have a diameter corresponding to a diameter of a lower part of the valve stem 22. For example, the first coupling guide 141 may be formed to be inclined toward an outer lower side to have a diameter which increases toward a lower end.

Meanwhile, at least one ring-shaped guide 145 may be formed on an inner circumferential surface of the first coupling guide 141 to prevent dirt, foreign substances, or bacteria in the outside and an upper space of the coupling cylinder 11 from being transferred to a lower space of the first coupling guide 141.

The second coupling guide 142 may be formed in a roughly cylindrical shape of which upper and lower surfaces are open and may be formed to have a diameter greater than that of the first coupling guide 141.

An upper end of the second coupling guide 142 may be inserted into a lower end of the elastic member 23 of the pumping part 20 to prevent a flow in a diameter direction and arbitrary separation of the elastic member 23. The connection member 143 may be formed in a cylindrical shape of which a lower surface is open.

An upper end of the housing 12 is coupled to a space between the connection member 143 and the second coupling guide 142. A fixing protrusion 144 configured to fix the upper end of the housing 12 may be formed on an inner circumferential surface of the connection member 143.

Further, the guide member 14 may partition an upper space and a lower space of the coupling cylinder 11 to prevent arbitrary transferring of the medication in the lower space of the coupling cylinder 11 to the upper space. In addition, a gasket 15 configured to fix the upper end of the housing 12 to the inside of the coupling cylinder 11 and seal a gap between the container and the upper space of the coupling cylinder 11 may be formed in a lower part of the guide member 14.

As shown in FIGS. 4 and 6A, 6B and 6C, the housing 12 may be formed in a pipe shape in which a diameter increases toward an upper part.

Figure 6A:
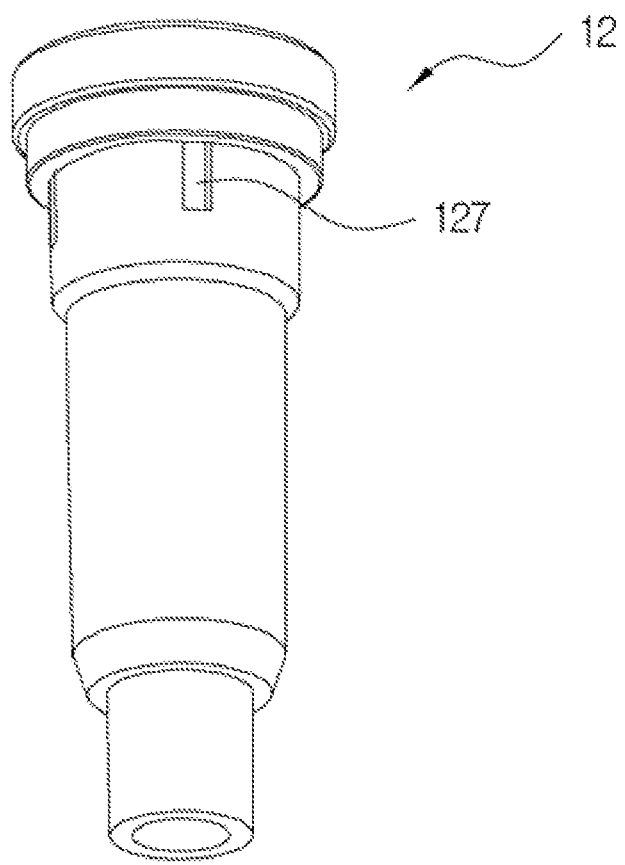
FIGS. 6A, 6B and 6C are views for describing a configuration of a housing according to the present disclosure.
Figure 6B:
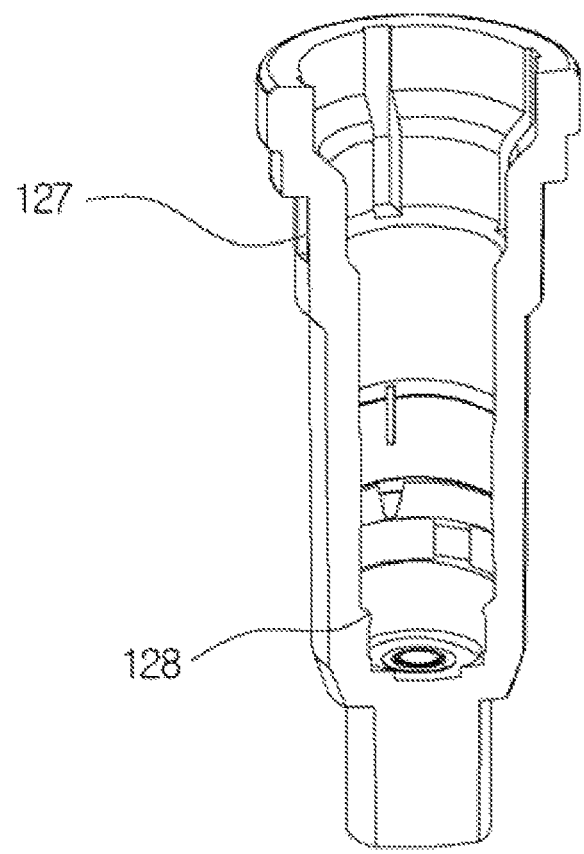
Figure 6C:
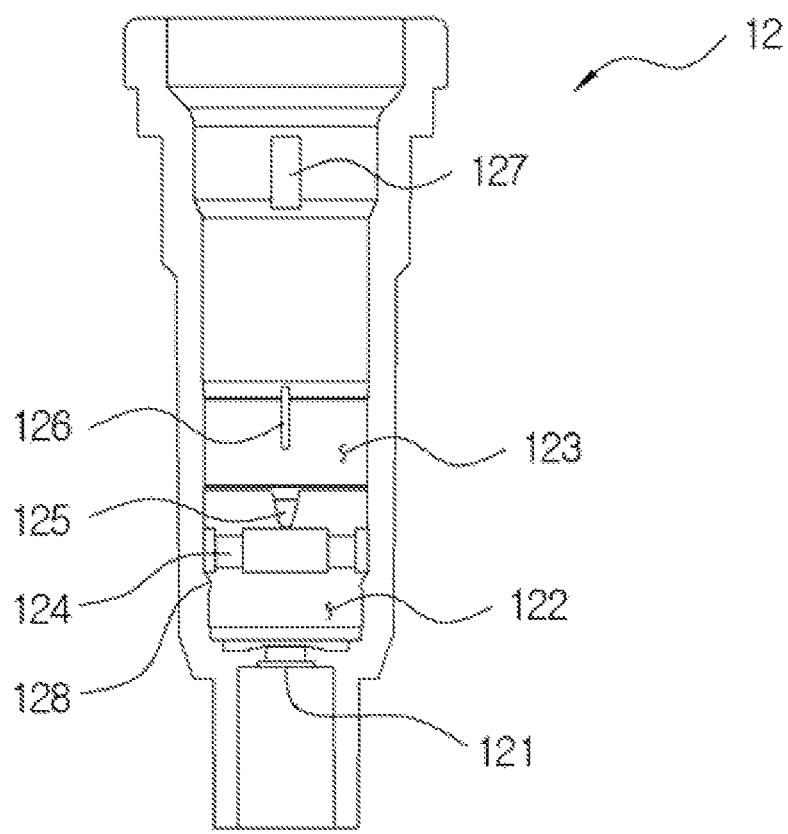

FIGS. 6A, 6B and 6C are views for describing a configuration of the housing 12 according to the present disclosure, wherein FIG. 6A is a perspective view of the housing 12, FIG. 6B is a view illustrating a configuration of the inside of the housing 12, and FIG. 6C is a cross-sectional view of the housing 12.

The introduction port 121 through which the medication stored in the container may be formed at the lower part of the housing 12, and a tube (not shown in the drawings) installed in the container and configured to suction the medication stored in the container may be connected to a lower end of the housing 12. An upper part of the housing 12 is fitted to a ring-shaped fixing protrusion 144.

As shown in FIGS. 6B and 6C, an installation space 122 in which the first check valve 13 is installed and a storage space 123 in which the medication introduced from the container is temporarily stored are provided in the housing 12. An amount of the medication discharged from the discharge part 30 may be determined according to a volume of the storage space 123.

An inner circumferential surface of the housing 12 is provided with a first adjusting groove 124, a second adjusting groove 125, and a third adjusting groove 126 configured to adjust an amount of the medication to be discharged and a pressure state during discharge when the medication exceeding a set amount to be discharged is introduced into the storage space 123. Further, as shown in FIGS. 6B and 6C, a ring-shaped protrusion 128 configured to fix the first check valve 13 is formed in an upper part of the installation space 122 and prevents movement of a main body of the first check valve 13 during a discharge process of the medication. As described above, since the movement of the main body of the first check valve 13 is prevented, noises generated during the discharge process of the medication may be prevented. Further, when the medication exceeding the set amount is introduced into the storage space 123, a recovery port 127 configured to discharge the medication exceeding the set amount to the outside of the housing 12 and recover the medication to the container may be formed in an upper part of the housing 12. As shown in FIG. 6A, the recovery port 127 is formed in a rectangular shape. Further, the above-described recovery port 127 may be provided with at least two recovery ports to quickly perform the discharge.

Meanwhile, as shown in FIGS. 6B and 6C, the first adjusting groove 124 is provided at the lower part of the housing 12 in a quadrangular shape. Four first adjusting grooves 124 are formed to be separated apart from each other at 90° intervals. Further, the second adjusting groove 125 is formed on the first adjusting groove 124 in an inverted triangle shape. Two second adjusting grooves 125 are formed to be separated apart from each other at 180° intervals. Further, the third adjusting groove 126 is provided on the second adjusting groove 125 in a straight shape. Two third adjusting grooves 126 are formed to be separated apart from each other at 180° intervals.

As described above, in the present disclosure, a pumping operation of the medication discharged by the pumping part 20 may be accurately performed and noise generation during pumping may be prevented by providing the first adjusting groove 124, the second adjusting groove 125, and the third adjusting groove 126 at different locations and shapes in the storage space 123 of the housing 12. That is, the medication may be discharged in an accurate amount from the discharge part 30.

Meanwhile, although FIGS. 6A, 6B and 6C show that the four first adjusting grooves 124 are formed and the two second adjusting grooves 125 and the two third adjusting grooves 126 are formed, the present disclosure is not limited thereto, and the number, the sizes, and the shapes of first adjusting grooves 124, the second adjusting grooves 125, and the third adjusting grooves 126 may be changed according to a discharge amount of the medication to be discharged.

Figure 7A:
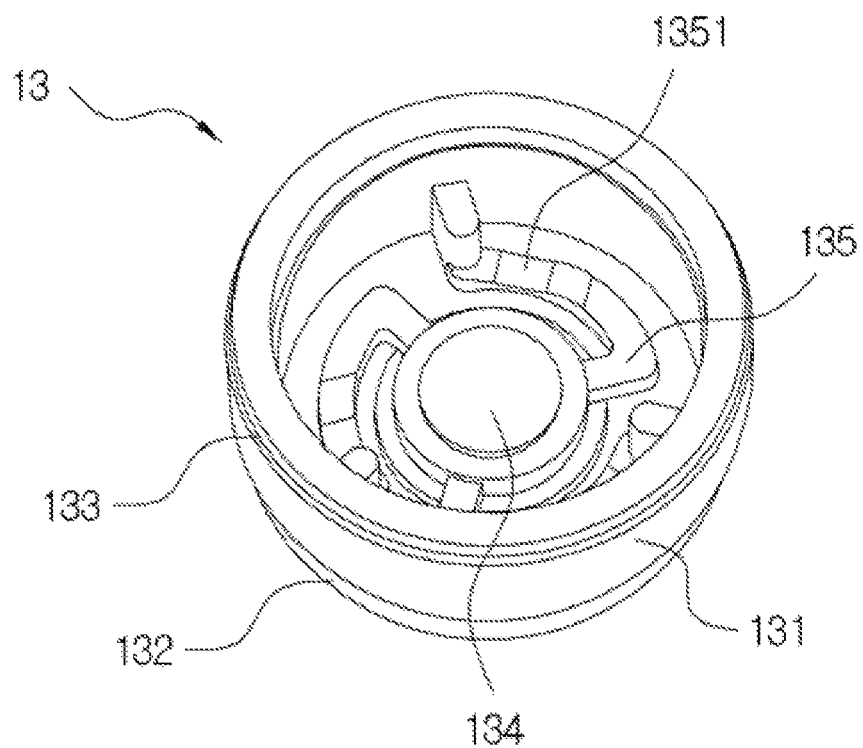
FIGS. 7A, 7B and 7C are views illustrating a configuration of a first check valve mounted in an installation space of the housing shown in FIGS. 6A, 6B and 6C.
Figure 7B:
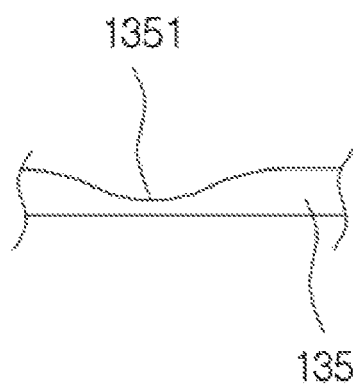
Figure 7C:
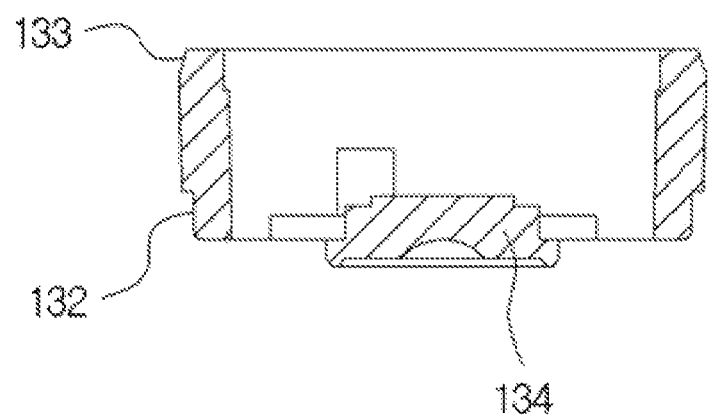

FIGS. 7A, 7B and 7C are views of the first check valve mounted in the installation space of the housing, wherein FIG. 7A is a perspective view, FIG. 7B is a cross-sectional view of a part of a connection rib, and FIG. 7C is a cross-sectional view.

The first check valve 13 is composed of a main body 131 having a roughly flat cylindrical shape of which an upper surface is open as shown in FIGS. 7A, 7B and 7C, a lower part of an outer periphery of the main body 131 is provided with a seating part 132 having steps to be seated in the installation space 122 of the housing 12 as shown in FIG. 7C, and an upper part of the outer periphery of the main body 131 is provided with a tapered part 133 to be fitted to the ring-shaped protrusion 128 provided on the installation space 122 of the housing 12.

In the first check valve 13 according to the present disclosure, by providing the tapered part 133, the main body 131 of the first check valve 13 is fixed to the installation space 122 during the pumping by a repetitive operation of the pumping part 20 so that an occurrence of a pumping error and the noise generation may be prevented.

Further, as shown in FIG. 7A, a valve sheet 134 configured to open or close the introduction port 121 is provided at an inner center portion in the first check valve 13, and the valve sheet 134 is connected to the main body 131 by a plurality of connection ribs 135.

Three connection ribs 135 are provided from the outside toward a center of the first check valve 13 so that the valve sheet 134 of the first check valve 13 may be smoothly elevated according to the elevation operation of the valve stem 22, and each of the connection ribs 135 is formed to be curved. Further, in the first check valve 13 according to the present disclosure, a concave part 1351 is provided at a center portion of an upper part of each of the connection ribs 135 for smooth descending of the valve sheet 134 during the pumping operation as shown in FIG. 7B.

As described above, since the valve sheet 134 smoothly ascends due to the concave part 1351 and a load is concentrated on the concave part 1351 and thus the valve sheet 134 descends while maintaining a balance by providing the concave part 1351 at each of the connection ribs 135, the pumping error may be prevented.

Meanwhile, although FIGS. 7A, 7B and 7C show that the three connection ribs 135 are formed, the present disclosure is not limited thereto, and two or at least four connection ribs 135 may be formed.

As shown in FIGS. 2 to 4 and FIGS. 8A and 8B, the pumping part 20 may include the valve stem 22 elevated according to an elevation operation of the discharge part 30 and the elastic member 23 coupled to the outside of the valve stem 22 to provide a restoring force to the discharge part 30.

Figure 8A:
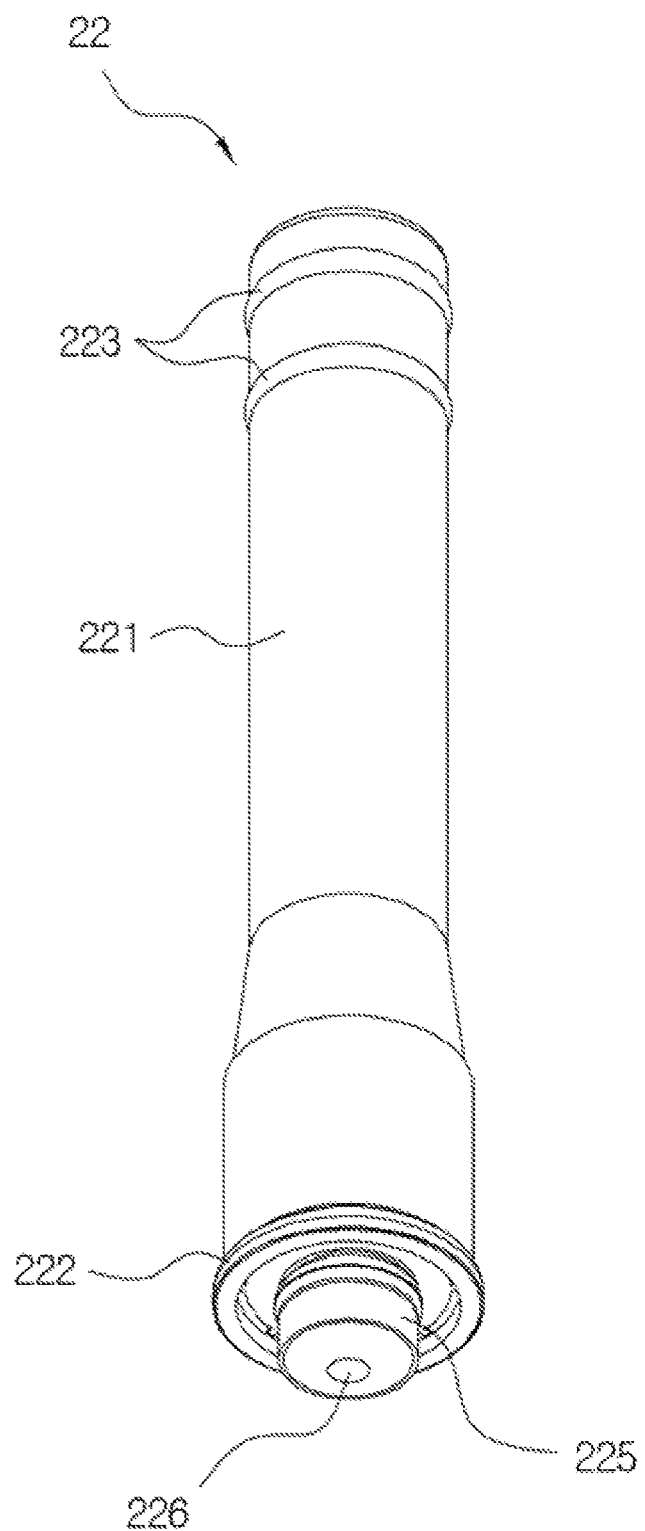
FIGS. 8A and 8B are views for describing a configuration of a valve stem according to the present disclosure.
Figure 8B:
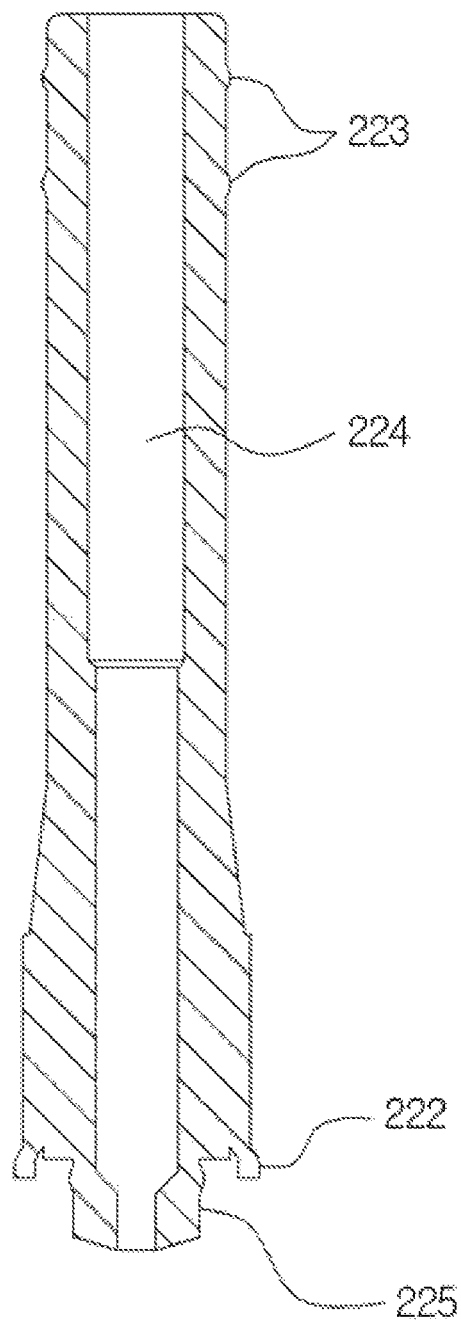

FIGS. 8A and 8B are views for describing a configuration of the valve stem according to the present disclosure, wherein FIG. 8A is a perspective view and FIG. 8B is a cross-sectional view.

The valve stem 22 serves to pump the medication temporarily stored in the storage space 123 of the housing 12 and transfer the medication to the discharge part 30 while being elevated in the storage space 123, and includes a body 221 formed in a cylindrical shape, a ring-shaped protrusion part 222 provided on a lower outer circumferential surface of the body 221, and a ring-shaped coupling part 223 provided on an upper outer circumferential surface of the body 221 to be coupled to the liner 32 as shown in FIG. 8A.

As shown in FIG. 8A, the body 221 is formed to have a diameter which increases toward a lower part of the body 221 so as to prevent movement of the medication by being in close contact with an inner circumferential surface of the first coupling guide 141 during an ascending operation of the valve stem 22 and to prevent introduction of external dirt, foreign substances, or bacteria into the medication stored in the storage space 123. The ring-shaped protrusion part 222 is provided to be in close contact with the inside of the housing 12 and be elevated in the housing 12 to prevent the medication from leaking to the outside of the body 221 during the pumping operation. Further, as shown in FIG. 8A, a pair of ring-shaped coupling parts 223 may be provided to solidly maintain a fitted state with the liner 32.

As shown in FIG. 8B, a first flow path 224 configured to transfer the medication from the storage space 123 to the discharge part 30 is provided in the body 221.

Further, a suction part 225 is provided to protrude from a lower center portion of the body 221, and a suction port 226 is provided at a center of the suction part 225. As shown in FIG. 8B, the suction part 225 is provided to have an outer diameter smaller than that of the body 221, and the suction port 226 is provided to have an inner diameter smaller than that of the first flow path 224. That is, in the valve stem 22 according to the present disclosure, since a pressure difference occurs between the inside of the first flow path 224 and the inside of the suction part 225 by providing the suction port 226 having an inner diameter smaller than that of each of the suction part 225 and the first flow path 224 unlike the related art, initial discharge of the medication provided in the storage space 123 may be certainly performed and the pumping error may be prevented.

The elastic member 23 is elastically transformed during a descending operation of the discharge part 30 and serves to provide the restoring force to the head base 31 provided in the discharge part 30. To this end, as shown in FIGS. 2 and 3, the lower end of the elastic member 23 may be supported by an upper surface of the connection member 143 of the coupling cylinder 11, and an upper end of the elastic member 23 may be supported by a support member of the head base 31.

As shown in FIGS. 2 to 5 and FIGS. 9 to 12, the discharge part 30 may include the head base 31 forming an exterior and elevated according to an operation of a user, the liner 32 installed in the head base 31 and configured to transfer the pumped medication to the discharge hole 312 of the head base 31, and a drop forming part configured to form a drop to discharge the medication so as to be transferred to the discharge hole 312 in a drop state.

Figure 9A:
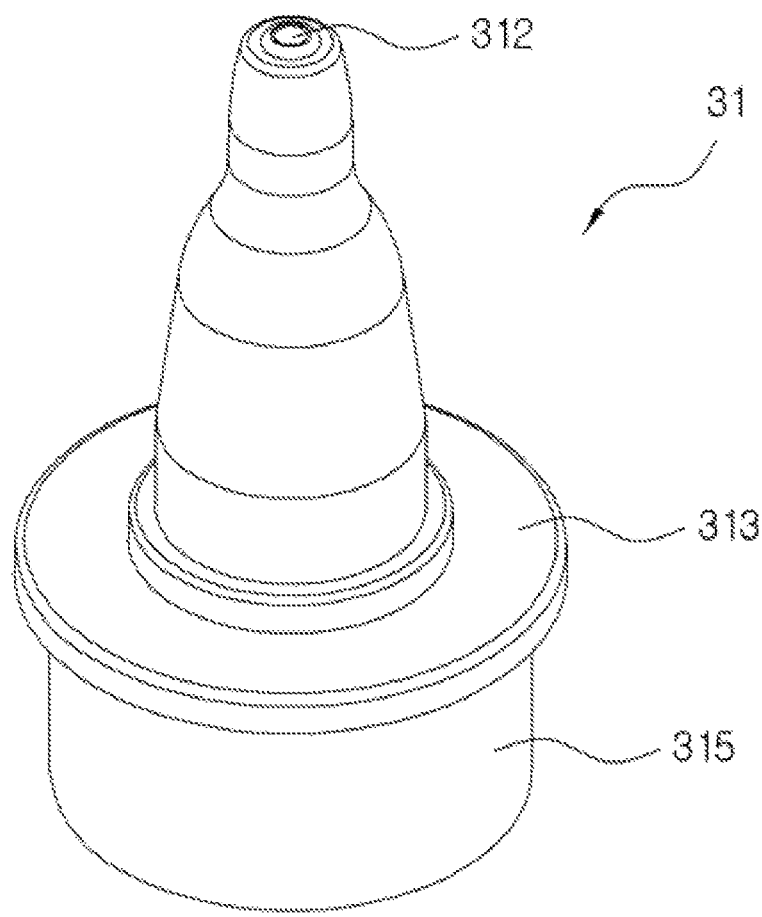
FIGS. 9A and 9B are views illustrating a configuration of a head base according to the present disclosure.
Figure 9B:
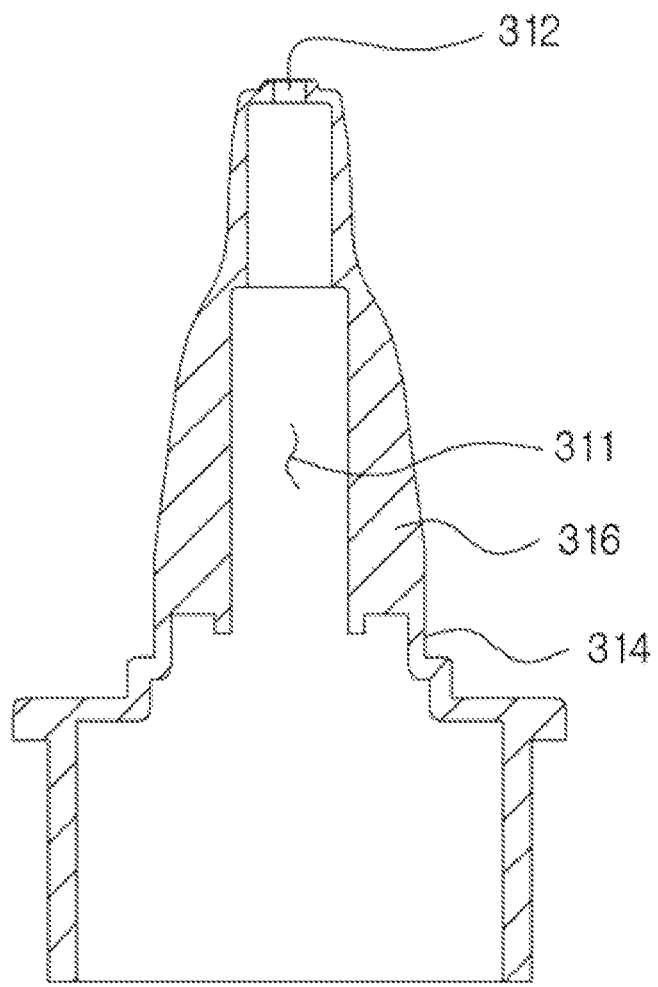

FIGS. 9A and 9B are views illustrating a configuration of the head base according to the present disclosure, wherein FIG. 9A is a perspective view of the head base 31, and FIG. 9B is a cross-sectional view of the head base 31.

As shown in FIG. 9A, the head base 31 is formed to have a diameter which decreases toward an upper end of the head base 31 to discharge the medication to an eyeball or the like of a human body.

The discharge hole 312 is formed in an upper end of the head base 31 to discharge the medication, and a flange 313 formed in a flat circular shape to be pressed and operated by the user and a vertical part 315 fitted to be capable of elevating at the outside of an upper end of the coupling cylinder 11 may be formed at a center portion of the head base 31.

Further, as shown in FIG. 9B, a coupling path 311 configured to couple the liner 32 is formed in the head base 31, a guide 314 for insertion of the liner 32 and a support member 316 configured to support the guide 314 are formed around the coupling path 311, and the liner 32 and the elastic member 23 are disposed in the guide 314.

A distance between a lower surface of the flange 313 and the upper end of the coupling cylinder 11 becomes an operation distance during elevation operations of the head base 31 and the valve stem 22. That is, the upper end of the coupling cylinder 11 may serve as a stopper.

Figure 10A:
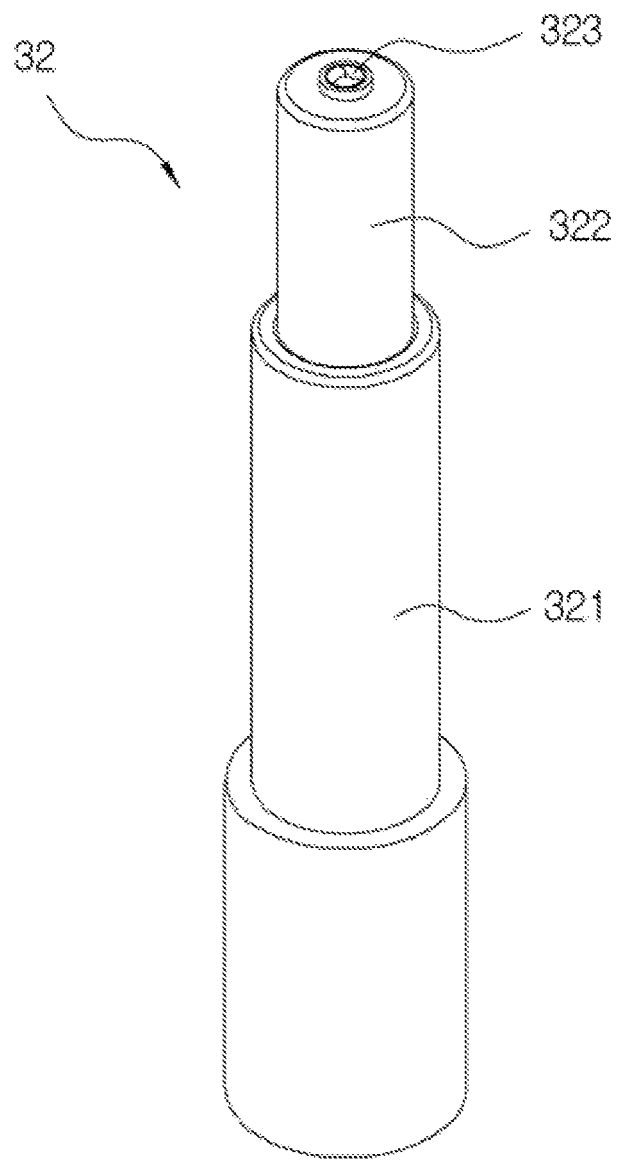
FIGS. 10A and 10B are views for describing a configuration of a liner according to the present disclosure.
Figure 10B:
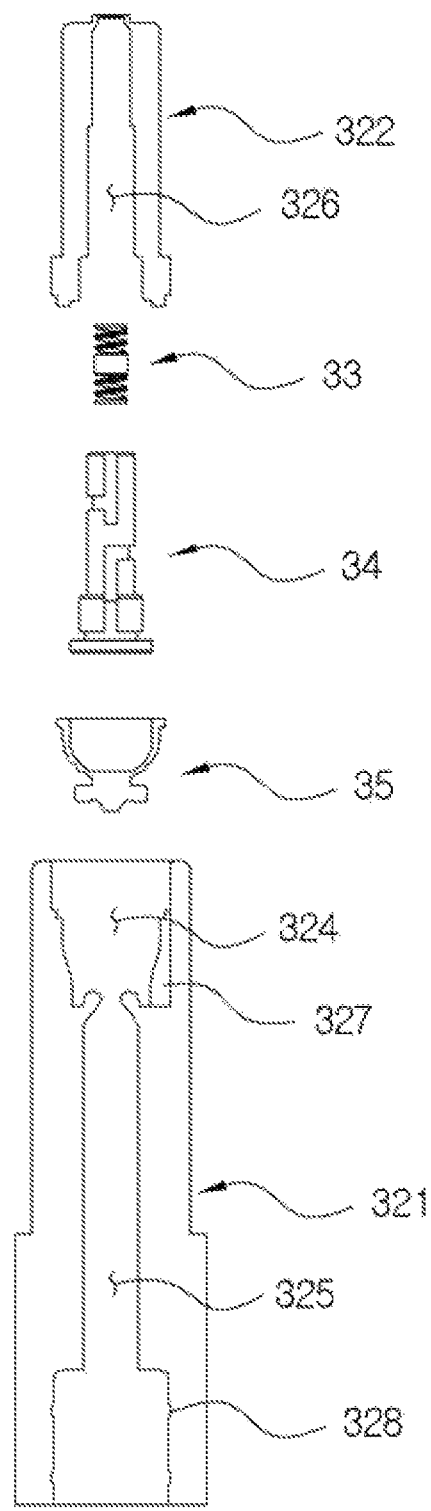

FIGS. 10A and 10B are views for describing a configuration of the liner according to the present disclosure, wherein FIG. 10A is a perspective view of the liner and FIG. 10B is an exploded cross-sectional view of the liner.

As shown in FIGS. 3 and 10A, the liner 32 includes a guide part 321 formed in a roughly cylindrical shape and into which the valve stem 22 is inserted, and a moving path part 322 formed to be stepped in a diameter smaller than that of the guide part 321 and fitted to the discharge hole 312 through the coupling path 311, and the discharge hole 323 is provided in an upper part of the moving path part 322. As described above, since the discharge hole 323 is directly provided in an end portion of the moving path part 322, permeation of foreign substances and bacteria may be minimized.

In the present disclosure, coupling between the liner 32 and the head base 31 may be easily implemented by simply fitting the guide part 321 and the moving path part 322 to the coupling path 311 during assembly of the liner 32 and the head base 31. As shown in FIG. 10B, a ring-shaped concave part 328 into which the ring-shaped coupling part 223 of the valve stem 22 is inserted is provided in a lower part of the guide part 321.

The discharge hole 323 is composed of three separation films each provided at 120° intervals and maintains a closed state when the medication dispenser is not used. Since center portions of the three separation films are opened by a discharge pressure of the medication during a discharge operation of the medication, the medication is discharged in the drop state. Since each of the three separation films provided in the discharge hole 323 returns to a closed state after the above-described discharge operation is completed, the permeation of the foreign substances and bacteria may be certainly prevented.

Further, a diameter of the discharge hole 323 may be set by an experimental value to discharge the medication in a predetermined amount. In addition, a plurality of drop forming grooves forming the drop to discharge the medication in the predetermined amount and in the drop state by reducing a discharge speed and a discharge pressure may be provided around the discharge hole 323. The discharge hole 323 discharges the medication transferred by an ascending operation of the second check valve 35 shown in FIG. 4 in the drop state during a descending operation of the head base 31.

In the embodiment, the discharge amount of the medication in one instance of discharge may be set to about 0.02 to 0.05 ml, preferably about 0.03 ml. Further, the diameter of the discharge hole 323 may be set to about 1.5 to 2.0 mm, preferably about 1.7 mm.

As shown in FIG. 10B, an upper part of the guide part 321 is fitted to the coupling path 311, and a second flow path 325 and an elevation space 324, in which the second check valve 35 shown in FIG. 4 is mounted, are provided in the guide part 321. A medication guide groove 327 for discharging the medication is formed in one side of the elevation space 324. Further, a flow path space 326, in which the pollution prevention member 33 and the flow path member 34 shown in FIG. 4 are mounted, is provided in the moving path part 322.

Figure 11A:
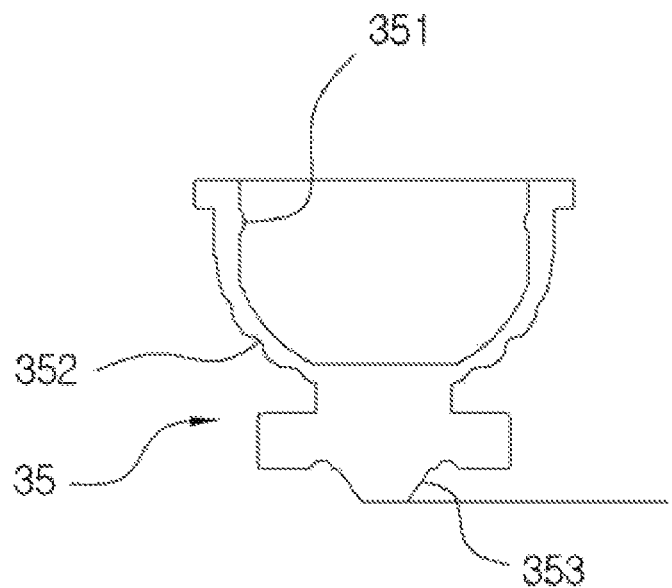
FIGS. 11A and 11B are views illustrating a configuration and an operation state of a second check valve mounted in an elevation space of the liner shown in FIGS. 10A and 10B.
Figure 11B:
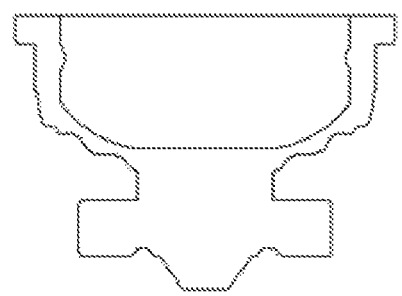

In addition, the second check valve 35 shown in FIG. 4 will be described according to FIGS. 11A and 11B. FIGS. 11A and 11B are views illustrating a configuration and an operation state of a second check valve mounted in an elevation space of the liner shown in FIGS. 10A and 10B, wherein FIG. 11A illustrates a normal state of the second check valve, and FIG. 11B illustrates a compressed state of the second check valve.

As shown in FIG. 11A, the second check valve 35 is mounted in the elevation space 324 of the guide part 321 of the liner, and composed of a hemispherical cylinder which has an open upper part, and a diameter which decreases toward a lower end. A ring-shaped engaging protrusion 351 configured to maintain the flow path member 34 is formed in the second check valve 35, a variable part 352 is provided in an outer circumferential part of the second check valve 35 so that the hemispherical cylinder is vertically variable by pressure, and an opening and closing protrusion 353 configured to perform supply and blocking of a flow path in the second flow path 325 is formed in a lower part of the second check valve 35. Meanwhile, as shown in FIG. 10B, the medication guide groove 327 configured to discharge the medication is provided between the second check valve 35 in the elevation space 324 and the second flow path 325 in the guide part 321.

Since the above-described second check valve 35 is formed of a soft synthetic resin material to be transformable and the variable part 352 is formed of a plurality of ring-shaped grooves over the entire circumference of the hemispherical cylinder, as shown in FIG. 11B, the plurality of ring-shaped grooves are folded upward and the opening and closing protrusion 353 moves in an upward direction when the second flow path 325 is open, and the plurality of ring-shaped grooves and the opening and closing protrusion 353 return to a state shown in FIG. 11A by an inherent elastic force of the variable part 352 itself when the second flow path 325 is closed.

As shown in FIG. 11A, the opening and closing protrusion 353 is formed in a wedge shape toward the second flow path 325 to close the second flow path 325.

As described above, in the present disclosure, a backflow of the medication may be certainly prevented and a structure may be simplified in comparison with the related art by applying the second check valve 35 in which the plurality of ring-shaped grooves provided in the variable part 352 are folded, and thus the opening and closing protrusion 353 moves in the upward direction when the second flow path 325 is open and the plurality of ring-shaped grooves and the opening and closing protrusion 353 return to an original state by the inherent elastic force of the variable part 352 itself when being closed, and since a spring is not used, a pumping sensation may be improved.

Further, the flow path member 34 shown in FIG. 10B will be described according to FIGS. 12A and 12B.

Figure 12A:
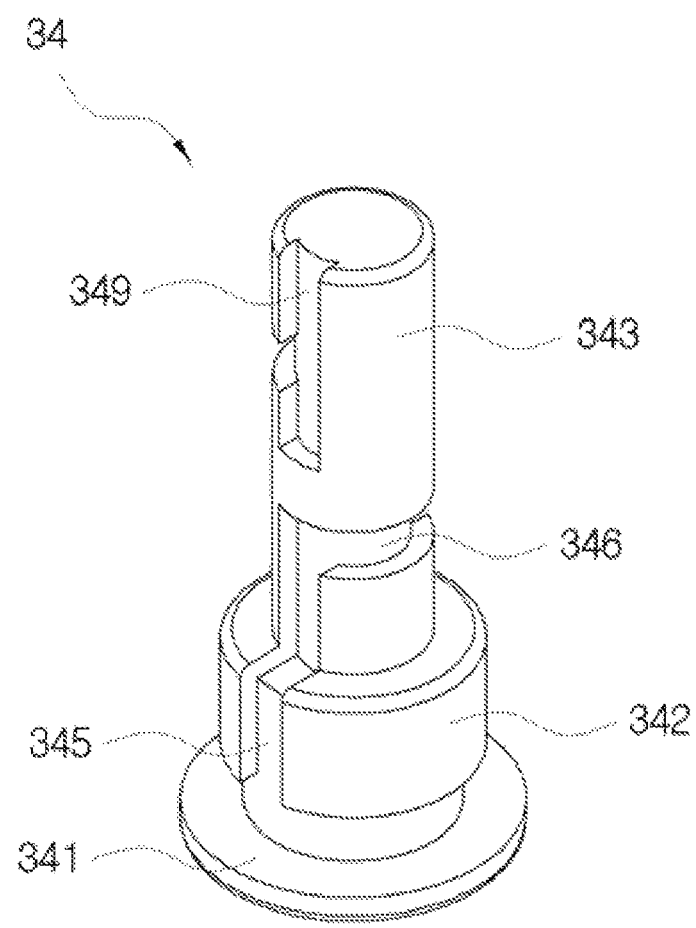
FIGS. 12A and 12B are views illustrating a configuration of a flow path member mounted in a flow path space of the liner shown in FIGS. 10A and 10B.
Figure 12B:
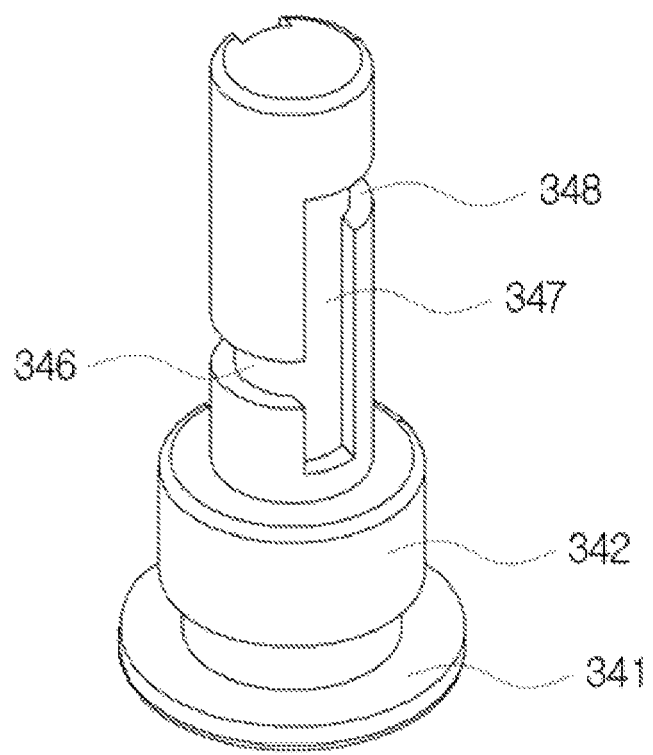

FIGS. 12A and 12B are views illustrating a configuration of the flow path member mounted in the flow path space of the liner shown in FIG. 10B.

According to the present disclosure, as shown in FIG. 3, the flow path member 34 is fitted to the flow path space 326 provided in the moving path part 322, and the pollution prevention member 33 is provided on the flow path member 34. The pollution prevention member 33 may be formed of, for example, a silver (Ag) spring.

As shown in FIGS. 12A and 12B, the flow path member 34 includes a supporting plate 341 formed in a disk shape to be engaged with the ring-shaped engaging protrusion 351 of the second check valve 35 at a bottom part of the flow path space 326, a first induction part 342 formed in a cylindrical shape on the supporting plate 341, and a second induction part 343 formed in a cylindrical shape on the first induction part 342. The first induction part 342 is formed to have an outer diameter smaller than that of the supporting plate 341, and the second induction part 343 is formed to have an outer diameter smaller than that of the first induction part 342.

As induction paths in the flow path member 34, a first induction path 345 for ascending of the medication is provided in a side surface of the first induction part 342 and a lower side surface of the second induction part 343, and a second induction path 346 configured to extend from the first induction path 345 is provided in a rotating direction along an outer circumferential surface of the second induction part 343 as shown in FIG. 12A, a third induction path 347 configured to extend from the second induction path 346 is provided upward in a side surface of the second induction part 343, a fourth induction path 348 configured to extend from the third induction path 347 is provided in a rotating direction along the outer circumferential surface of the second induction part 343, and a fifth induction path 349 configured to extend from the fourth induction path 348 is provided upward in the side surface of the second induction part 343 as shown in FIG. 12B. Meanwhile, a lower part of the third induction path 347 is provided to extend downward from the second induction path 346 as shown in FIG. 12B, and a lower part of the fifth induction path 349 is provided to extend downward from the fourth induction path 348 as shown in FIG. 12A.

The medication which passes through the fifth induction path 349 is discharged to the discharge hole 323 through the pollution prevention member 33.

Meanwhile, as shown in FIG. 3, the flow path member 34 is provided with a space part therein to reduce its own weight and allow an operation with the second check valve 35 to be flexible.

As described above, since the first to fifth induction paths 345 to 349 are provided in the flow path member 34 according to the present disclosure, the backflow of the medication may be prevented, and permeation of the external dirt, the foreign substances, or the bacteria to the container may be prevented even when the external dirt, the foreign substances, or the bacteria are introduced through the discharge hole 323.

Accordingly, the present disclosure may completely prevent introduction of the external dirt, the foreign substances, or the bacteria which permeate from the outside of the medication dispenser to the medication stored in the medication dispenser.

Figure 13A:
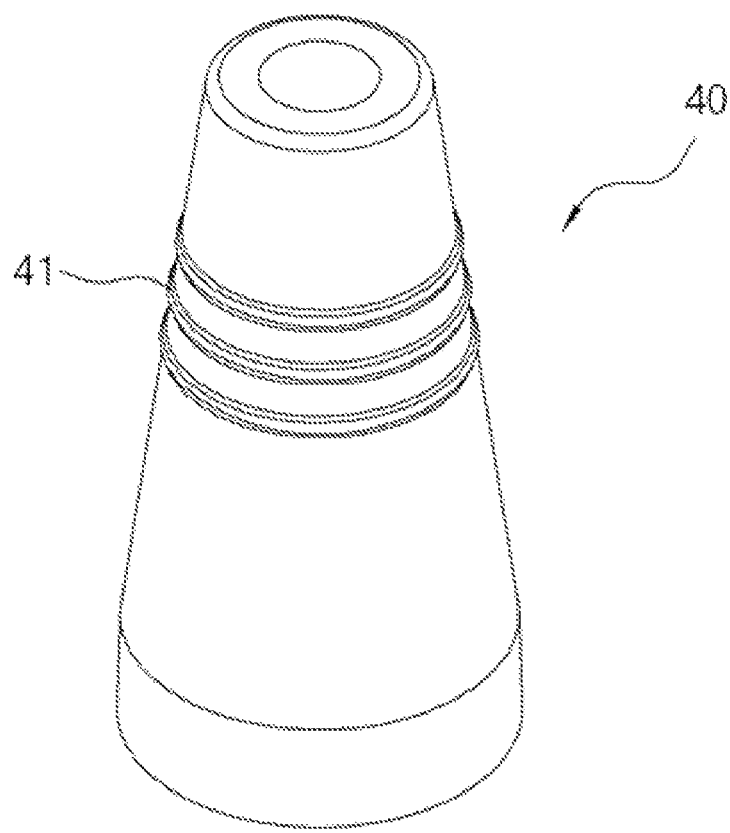
FIGS. 13A and 13B are views illustrating a configuration of a cover part according to the present disclosure.
Figure 13B:
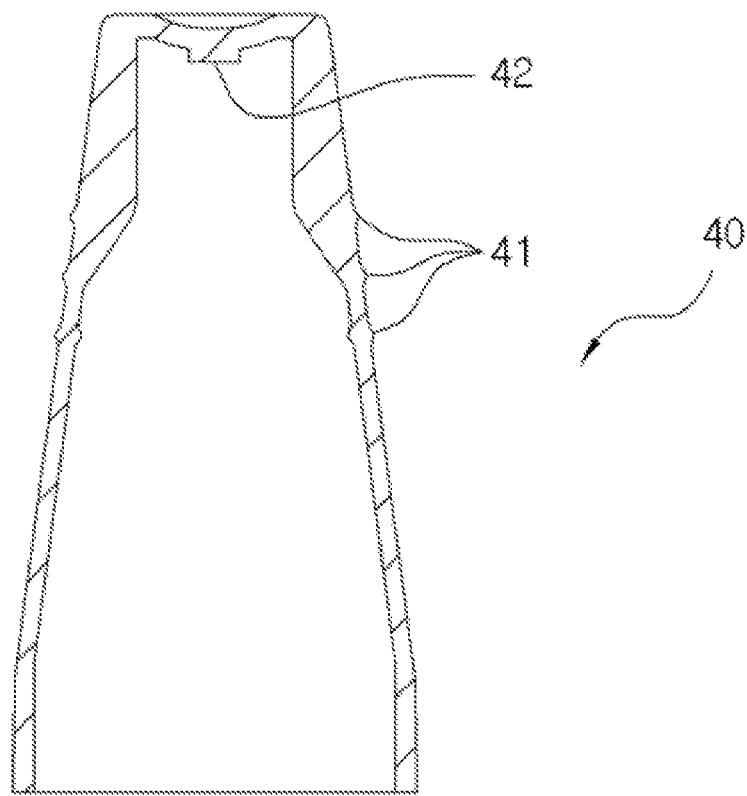

Further, a structure of the cover part according to the present disclosure will be described according to FIGS. 13A and 13B. FIGS. 13A and 13B are views illustrating a configuration of the cover part according to the present disclosure.

The cover part 40 is formed in a shape the same as that of the head base 31. A plurality of ring-shaped engaging parts 41 are formed on an outer circumference of the cover part 40 as shown in FIG. 13A to allow the user to easily perform insertion and withdrawal at the head base 31 with his or her hands, and an insertion part 42 formed to protrude from a center portion of the cover part 40 to seal the discharge hole 312 of the head base 31 is provided on an upper part of the inside of the cover part 40 as shown in FIG. 13B.

Accordingly, the discharge of the medication to the discharge hole 312 may be prevented by fitting the cover part 40 to the head base 31.

Further, a coupling relation of the medication dispenser having a bacteria infiltration prevention function according to the present disclosure will be described.

First, the liner 32 shown in FIG. 10A is provided by mounting the second check valve 35 in the elevation space 324 provided in the guide part 321 of the liner 32 shown in FIG. 10B, inserting the pollution prevention member 33 formed of the Ag spring into the lower part of the moving path part 322 in which the discharge hole 323 is formed and then inserting the flow path member 34 into the moving path part 322 with the pollution prevention member 33, and fitting the moving path part 322 to the upper part of the guide part 321.

Further, the first coupling guide 141 passes through the coupling cylinder 11 and is coupled to the valve stem 22 in a state in which the valve stem 22 is located at the lower part of the coupling cylinder 11, the elastic member 23 is inserted into an upper part of the valve stem 22, and the ring-shaped coupling part 223 of the valve stem 22 is inserted into the ring-shaped concave part provided in the guide part 321.

In addition, coupling of the head base 31, the liner 32, and the valve stem 22 is completed by simply fitting the ring-shaped guide part 321 and the moving path part 322 to the coupling path 311 of the head base 31.

In this case, an upper end of the elastic member 23 is supported by the lower surface of the support member 316 of the head base 31, and the lower end of the elastic member 23 is supported by an upper surface of the connection member 143 of the coupling cylinder 11 and engaged with and fixed to the upper end of the second coupling guide 142.

Accordingly, the elastic member 23 may be stably fixed by the second coupling guide 142 and may be elastically transformed to provide the restoring force to the head base 31 when the head base 31 descends.

Further, the tapered part 133 of the first check valve 13 is fitted through the ring-shaped protrusion 128 provided on the installation space 122 of the housing 12, the upper end of the housing 12 is coupled to a space between the second coupling guide 142 and the connection member 143 of the coupling cylinder 11, and the gasket 15 is coupled to the coupling cylinder 11 to solidly fix the housing 12 and the coupling cylinder 11.

As described above, assembly is completed by coupling a tube to a lower end of the assembled medication dispenser and coupling the coupling cylinder 11 to an upper end of the container.

Further, a method of operating the medication dispenser according to the present disclosure will be described in detail with reference to FIGS. 2 and 12 and FIGS. 14 to 17.

Figure 14:
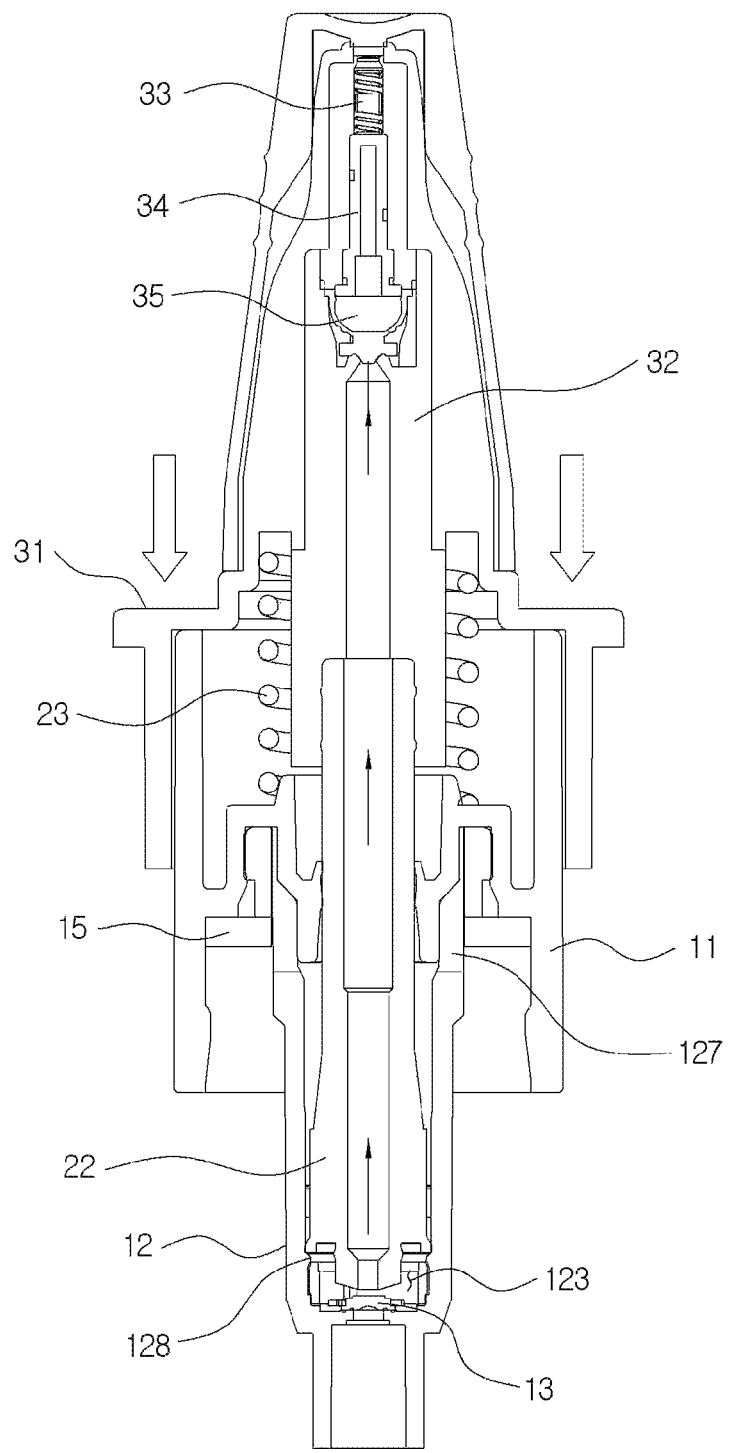
FIG. 14 is a cross-sectional view of a state in which the head base of the medication dispenser shown in FIG. 3 descends.
Figure 15A:
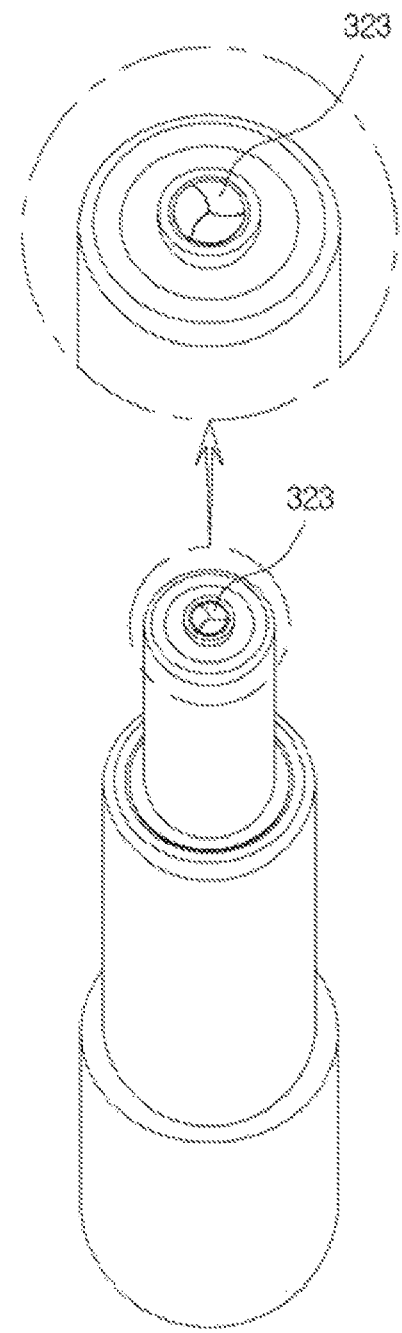
FIGS. 15A and 15B are views illustrating an operation state of a discharge hole provided in the liner.
Figure 15B:
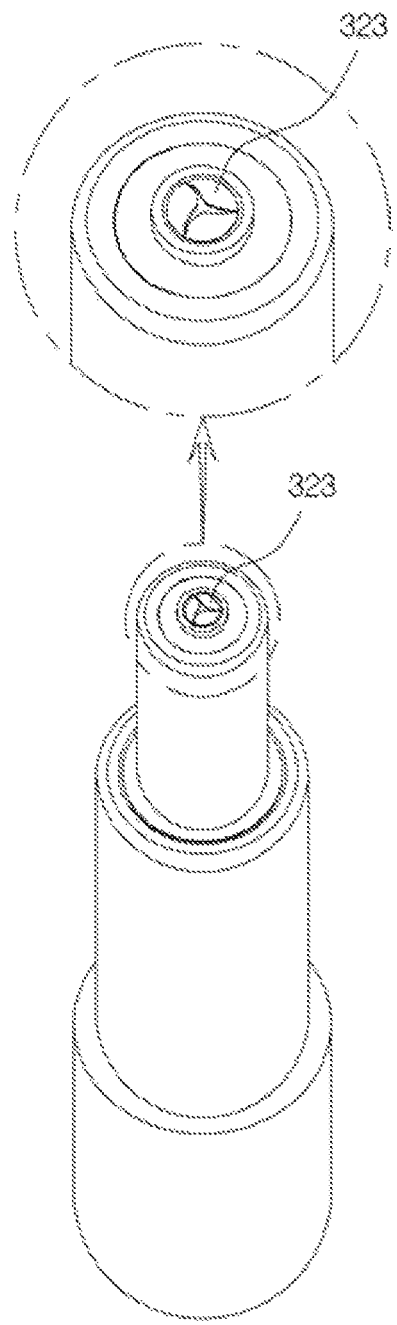

FIG. 14 is a cross-sectional view of a state in which the head base of the medication dispenser shown in FIG. 3 descends, and FIGS. 15A and 15B are views illustrating an operation state of the discharge hole provided in the liner, wherein FIG. 15A illustrates a state in which the discharge hole is closed, and FIG. 15B illustrates a state in which the medication is discharged from the discharge hole.

Figure 16A:
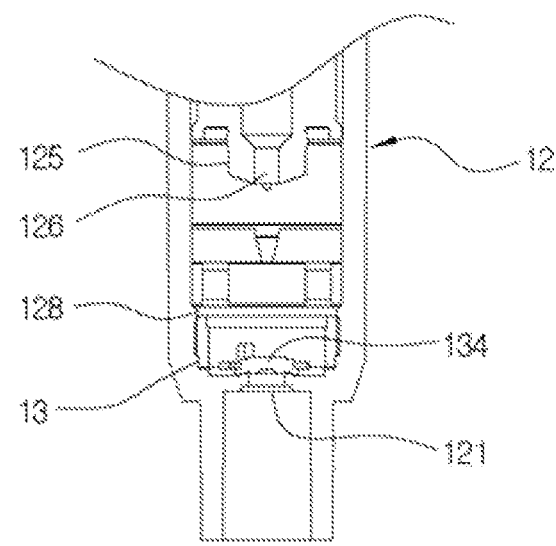
FIGS. 16A, 16B and 16C are views for describing an operation of the first check valve according to an operation of the valve stem in the medication dispenser having a bacteria infiltration prevention function according to the present disclosure.
Figure 16B:
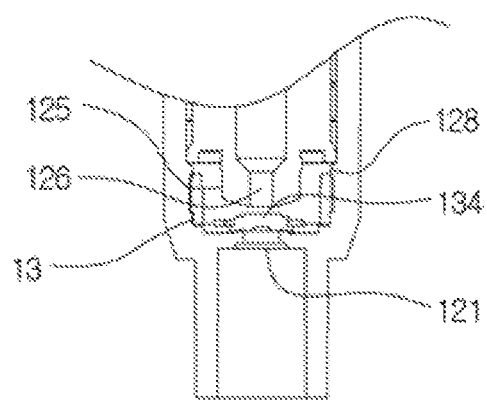
Figure 16C:
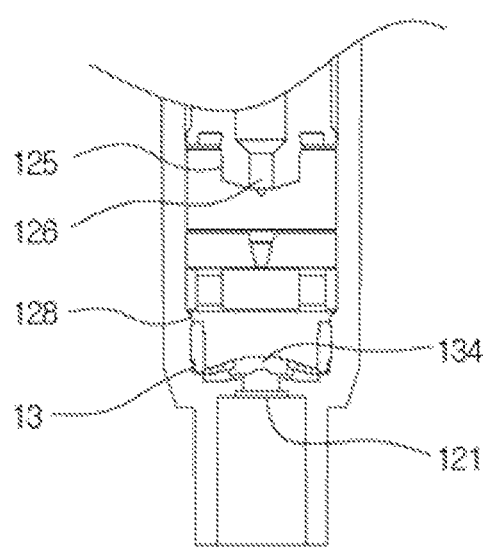

Further, FIGS. 16A, 16B and 16C are views for describing an operation of the first check valve according to an operation of the valve stem in the medication dispenser according to the present disclosure, wherein FIG. 16A illustrates a state in which the medication is maintained in the storage space 123, FIG. 16B illustrates a state in which the flange 313 is pressed to discharge the medication and thus the housing 12 is maintained to be closed to the first check valve 13, and FIG. 16C illustrates a state in which the valve sheet 134 of the first check valve 13 is open after discharging the medication.

Figure 17A:
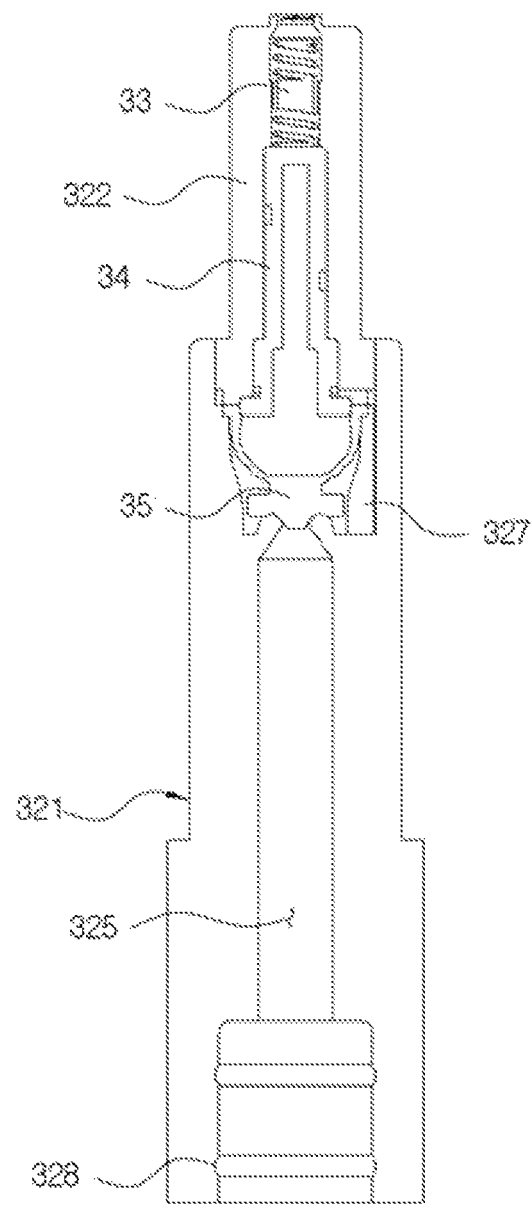
FIGS. 17A and 17B is a view for describing a process of discharging the medication from the medication dispenser having a bacteria infiltration prevention function according to the present disclosure.
Figure 17B:
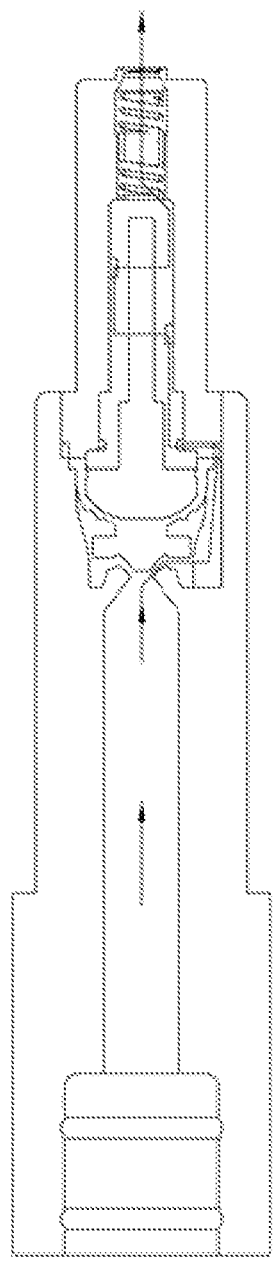

In addition, FIGS. 17A and 17B are views for describing a process of discharging the medication from the medication dispenser according to the present disclosure, wherein FIG. 17A illustrates a state in which the second check valve 35 closes the second flow path 325 and thus the medication is maintained in the storage space 123, and FIG. 17B illustrates a state in which the second check valve 35 opens the second flow path 325 and thus the medication is discharged to the discharge hole 323.

First, as shown in FIG. 17A, the second check valve 35 maintains an original state to close an upper end of the second flow path 325 provided in the guide part 321 of the liner 32 before being pressed by the user. Further, since a space in the second check valve 35 composed of a hemispherical cylinder and a space provided in the flow path member 34 communicate with each other and are maintained in a closed state, a variable operation at the variable part 352 of the second check valve 35 is very flexibly performed.

In addition, the ring-shaped protrusion part 222 of the valve stem 22 is in close contact with an inner surface of the first coupling guide 141 of the coupling cylinder 11 and an inner surface of the housing 12 to prevent movement of the medication toward an upper space of the coupling cylinder 11 or introduction of the external dirt, the foreign substances, or the bacteria into the housing 12.

As described above, the present disclosure may be used as a medication dispenser, without a preservative, which prevents pollution and decomposition of a medicine by completely preventing pollution of the medication stored in the medication dispenser having a bacteria infiltration prevention function.

Accordingly, since the preservative does not have to be added in a process of manufacturing the medication in the present disclosure, the time and material cost required during a process of manufacturing the medicine may be reduced, and an adverse effect which affects due to addition of the preservative may be prevented in advance.

As shown in FIG. 14, when the user removes the cover part 40 and presses the flange 313 of the head base 31, and thus the head base 31 descends, as shown in FIGS. 16A and 16B, the valve stem 22 becomes close to the tapered part 133 of the first check valve 13 while descending toward the storage space 123. That is, the suction port 226 provided in the suction part 225 of the valve stem 22 descends to a part close to an upper part of the valve sheet 134. In this case, the valve sheet 134 of the first check valve 13 moves in a downward direction due to a pressure generated in the installation space 122 corresponding to descending of the valve stem 22 to close the introduction port 121 of the housing 12.

Accordingly, the medication stored in the storage space 123 of the housing 12 is suctioned to the suction port 226 formed in the valve stem 22, and, as shown in FIG. 17B, the medication moves toward the discharge part 30 along the first flow path 224 and the second flow path 325 in the guide part 321.

In this case, as shown in FIG. 16B, since the suction port 226 of the valve stem 22 may descend to a location close to the upper part of the valve sheet 134 of the first check valve 13 and an inlet of the suction port 226 is formed to be very small, and thus a suction pressure may be greater than that of the related art, initial discharge is certainly performed and the pumping error may be prevented. Further, as shown in FIGS. 16A and 16B, the pumping operation with respect to the medication may be accurately performed, and the noise generation may be prevented by providing the first adjusting groove 124 in a lower part of the inner circumferential surface of the housing 12, providing the second adjusting groove 125 on the first adjusting groove 124 in the inverted triangle shape, and providing the third adjusting groove 126 on the second adjusting groove 125 in the straight shape.

As described above, as shown in FIGS. 11B and 17B, the variable part 352 of the second check valve 35 is transformed in an upward direction, that is, the variable part 352, in which the plurality of ring-shaped grooves are folded by the pressure of the medication which moves along the first flow path 224 of the valve stem 22 and the second flow path 325 in the guide part 321, and thus the second flow path 325 is opened.

Accordingly, as shown in FIG. 17B, the medication is guided to the supporting plate 341 of the flow path member 34 through the medication guide groove 327 provided between the second check valve 35 and the second flow path 325 in the guide part 321, guided to the pollution prevention member 33 through the first induction path 345 to the fifth induction path 349, and discharged in the drop state through the discharge hole 323 as shown in FIG. 15B.

That is, the medication guided to the supporting plate 341 of the flow path member 34 ascends along the first induction path 345 provided in the side surface of the first induction part 342 and the lower side surface of the second induction part 343, primarily rotates in a circumferential direction of the second induction part 343 along the second induction path 346, ascends along the third induction path 347 provided in the side surface of the second induction part 343, secondly rotates in the circumferential direction of the second induction part 343 along the fourth induction path 348, and ascends along the fifth induction path 349 provided in the upper side surface of the second induction part 343 to be guided to the pollution prevention member 33, and thus the discharge hole 323 is opened and the medication is discharged in the drop state as shown in FIG. 15B.

In this case, the amount of the medication discharged when the head base 31 descends once may be adjusted by the volume of each of the storage space 123 formed in the housing 12 and the first to third adjusting grooves 124, 125, and 126, the diameter of the discharge hole 323 formed in the liner 32, and the like.

As described above, in the medication dispenser having a bacteria infiltration prevention function according to the present disclosure, the first to fifth induction paths 345 to 349 may be provided in the flow path member 34, the backflow of the medication may be prevented by the three separation films each provided at 120° intervals, and the permeation of the external dirt, the foreign substances, or the bacteria to the container may be prevented even when the external dirt, the foreign substances, or the bacteria are introduced through the discharge hole 323. That is, the discharge hole 323 maintains the closed state when the medication dispenser is not used, as shown in FIG. 15A, and since the center portions of the three separation films are open during the discharge operation of the medication, the medication is discharged in the drop state as shown in FIG. 15B.

Further, when the pressure of a gap decreases while the medication is discharged, the variable part 352 of the second check valve 35 is restored to the state shown in FIG. 11A by the inherent elastic force so as to close the upper end of the second flow path 325 of the liner 32.

Further, when an operating force applied to the flange 313 is released, since the head base 31 ascends due to the restoring force of the elastic member 23, the valve stem 22 also ascends as in the state shown in FIG. 16A.

In this case, since a suction force is generated from the storage space 123 in the housing 12, as shown in FIG. 16C, the valve sheet 134 of the check valve 13 ascends to open the introduction port 121, and the medication stored in the container is introduced into and stored in the housing 12 through the tube and the introduction port 121. Meanwhile, since the first check valve 13 maintains a state in which the tapered part 133 is fitted to the ring-shaped protrusion 128 provided on the installation space 122, the main body 131 is solidly maintained in the installation space 122 when the valve sheet 134 ascends, and thus the occurrence of the pumping error and the noise generation during the pumping operation shown in FIGS. 16A to 16C may be prevented.

Meanwhile, when the medication is introduced into the housing 12 at an amount exceeding the predetermined amount, the medication exceeding the predetermined amount is recovered to the container through the recovery port 127 of the housing 12.

Further, the user presses the flange 313 a number of times that the medication is to be discharged, and the medication dispenser repeatedly performs the above-described processes to discharge the medication.

Accordingly, the present disclosure may discharge the liquid state medication stored in the container in the drop state in the predetermined amount and may prevent the introduction of external dirt, foreign substances, or bacteria into the medication stored in the medication dispenser.

As described above, in a medication dispenser having a bacteria infiltration prevention function according to the present disclosure, a back flow of a medication can be prevented and a pumping sensation can be improved by providing a flow path member and a second check valve in a liner. Further, the back flow of the medication can be prevented by providing a first induction path to a fifth induction path in a first induction part and a second induction part, and external dirt, foreign substances, or bacteria can be prevented from permeation into a container even when being introduced through a discharge hole.

In addition, in the medication dispenser having a bacteria infiltration prevention function according to the present disclosure, a pumping operation with respect to the medication to be discharged can be accurately performed and generation of noises can be prevented by providing a first adjusting groove, a second adjusting groove, and a third adjusting groove, which are configured to adjust an amount of the medication to be discharged and a pressure state during discharge, in an inner circumferential surface of a housing.

In addition, in the medication dispenser having a bacteria infiltration prevention function according to the present disclosure, since a load is concentrated on a concave part of a first check valve, and a valve sheet of the first check valve maintains a balance and is elevated by providing the concave part at a center portion of an upper part of a connection rib of the first check valve and fixing a main body of the first check valve to the housing, a pumping error can be prevented and noises according to movement of the first check valve can also be prevented.

As described above, although the present disclosure disclosed by an inventor is specifically described according to the embodiment, the present disclosure is not limited to the embodiment and may be variously changed without departing from a spirit of the present disclosure.

That is, the medication is used to describe the embodiment, but the present disclosure is not certainly limited thereto. For example, the present disclosure may be applied to fluid dispensers having various shapes and purposes and configured to discharge a liquid state fluid such as food or cosmetics in addition to the medication in a drop state.

What is claimed is:

1. A medication dispenser having a bacteria infiltration prevention function, comprising:
   a suction part coupled to an upper part of a container and configured to suction a liquid state medication stored in the container;
   a pumping part coupled to one side of the suction part to perform a pumping operation to discharge the medication in a predetermined amount;
   a discharge part installed on an upper end of the pumping part and having a discharge hole configured to discharge the medication in a drop state in a front end thereof; and
   a cover part configured to cover the discharge part,
   wherein the discharge part includes a head base into which the cover part is inserted and a liner inserted into the head base and to which an upper part of a valve stem is fitted, wherein the suction part includes a coupling cylinder coupled to an upper end of the container, a housing coupled to a lower part of the coupling cylinder, and a first check valve installed at a lower part of the housing to open and close an introduction port in which the medication is introduced into the housing, wherein a valve sheet configured to open or close the introduction port is provided at a center portion of an inside of the first check valve and connected to a main body by a plurality of connection ribs each provided with a concave part at a center portion of an upper part thereof, wherein the liner has a flow path member and a second check valve mounted therein and a discharge hole including three separation films each formed at an interval of 120° is provided in an upper part of the liner, wherein the second check valve is composed of a hemispherical cylinder mounted in an elevation space of the liner, having an open upper part, and of which a diameter decreases toward a lower end, and includes a variable part in which the hemispherical cylinder is vertically variable and an opening and closing protrusion configured to perform supply and blocking of a flow path, wherein the flow path member is provided with a supporting plate formed in a disk shape to be engaged with a ring-shaped engaging protrusion of the second check valve at a bottom part of a flow path space of the liner, a first induction part provided on the supporting plate in a cylindrical shape, and a second induction part provided on the first induction part in a cylindrical shape, and wherein first to fifth induction paths are provided in the first induction part and the second induction part. to fifth induction paths are provided in the first induction part and the second induction part.

2. The medication dispenser of claim 1, wherein:

the first induction path is provided at a side surface of the first induction part and a lower side surface of the second induction part for ascending of the medication;

the second induction path extends from the first induction path and is provided in a rotating direction along an outer circumferential surface of the second induction part;

the third induction path extends from the second induction path and is provided upward in a side surface of the second induction part;

the fourth induction path extends from the third induction path and is provided in the rotating direction along the outer circumferential surface of the second induction part; and the fifth induction path extends from the fourth induction path and is provided upward in the side surface of the second induction part.

3. The medication dispenser of claim 2, wherein:

when the medication exceeding a set amount to be discharged is introduced into a storage space, a first adjusting groove, a second adjusting groove, and a third adjusting groove configured to adjust an amount of the medication to be discharged and a pressure state during discharge are provided in an inner circumferential surface of the housing;

the first adjusting groove is provided in a lower part of the inner circumferential surface of the housing in a quadrangular shape;

the second adjusting groove is provided on the first adjusting groove in an inverted triangle shape; and the third adjusting groove is provided on the second adjusting groove in a straight shape.

4. The medication dispenser of claim 3, wherein:

a ring-shaped protrusion is provided on the inner circumferential surface of the housing, and a tapered part fitted to the ring-shaped protrusion is provided in the first check valve; and a main body of the first check valve is fixed to the housing during a pumping operation, and only the valve sheet is elevated.

5. The medication dispenser of claim 2, wherein:

the suction part is provided to protrude from a center portion of a lower end of the valve stem; and a suction port is provided in a center of the suction part.

* * * * *